United States Patent
Gundert et al.

(10) Patent No.: US 11,638,819 B2
(45) Date of Patent: May 2, 2023

(54) SIGNAL GENERATORS FOR USE WITH TISSUE MODIFICATION SYSTEMS

(71) Applicant: Galary, Inc., San Carlos, CA (US)

(72) Inventors: Timothy J. Gundert, Discovery Bay, CA (US); Paul B. Friedrichs, Belmont, CA (US)

(73) Assignee: Galvanize Therapeutics, Inc., Redwood City, CA (US)

( * ) Notice: Subject to any disclaimer, the term of this patent is extended or adjusted under 35 U.S.C. 154(b) by 69 days.

(21) Appl. No.: 17/227,232

(22) Filed: Apr. 9, 2021

(65) Prior Publication Data
US 2022/0080191 A1 Mar. 17, 2022

Related U.S. Application Data

(60) Provisional application No. 63/077,022, filed on Sep. 11, 2020.

(51) Int. Cl.
*G01R 31/56* (2020.01)
*A61N 1/08* (2006.01)
(Continued)

(52) U.S. Cl.
CPC .............. *A61N 1/08* (2013.01); *G01R 31/00* (2013.01); *G01R 31/56* (2020.01); *H03K 5/01* (2013.01); *G01R 31/327* (2013.01)

(58) Field of Classification Search
CPC . A61N 1/08; A61N 1/00; G01R 31/00; G01R 31/56; G01R 31/50; G01R 31/64;
(Continued)

(56) References Cited

U.S. PATENT DOCUMENTS 5,833,710 A 11/1998 Jacobson
9,987,081 B1 * 6/2018 Bowers ................. A61B 18/12
(Continued)

FOREIGN PATENT DOCUMENTS

EP 2777579 A1 9/2014
WO WO2014/025394 A1 2/2014
(Continued)

OTHER PUBLICATIONS

International Search Report & The Written Opinion of the International Searching Authority dated Aug. 16, 2021, International Application No. PCT/US2021/030911.

*Primary Examiner* — Natalie Huls
*Assistant Examiner* — James I Burris
(74) *Attorney, Agent, or Firm* — Vierra Magen Marcus LLP

(57) ABSTRACT

Embodiments described herein relate to signal generators, systems including signal generators, and related methods. A signal generator includes capacitor(s) to store energy used to generate a treatment signal. The signal generator also includes a waveform shaping circuit, a controller, a voltage sense circuit, and a current sense circuit. The waveform shaping circuit is coupled to the capacitor(s) and includes first, second, third, and fourth switches, each of which is configured to be selectively turned ON and OFF, to allow current to pass through the switch when turned ON, and to prevent current from passing through the switch when turned OFF. The controller selectively controls the switches in order to generate the treatment signal. The controller also selectively controls the switches in order to perform certain fault tests, which rely on voltages sensed by the voltage sense circuit and currents sensed by the current sense circuit.

22 Claims, 9 Drawing Sheets

(51) Int. Cl.
*H03K 5/01* (2006.01)
*G01R 31/00* (2006.01)
*G01R 31/327* (2006.01)

(58) Field of Classification Search
CPC .. G01R 31/62; G01R 31/327; G01R 31/3275;
G01R 31/3277; H03K 5/01; H03K 5/026;
H03K 5/04; H03K 17/30; H03K 5/084;
A61B 2018/1286; A61B 18/1233; A61B
18/12
See application file for complete search history.

(56) References Cited

U.S. PATENT DOCUMENTS

| | | |
|---|---|---|
| 10,016,232 B1 | 7/2018 | Bowers et al. |
| 10,322,286 B2 | 6/2019 | Viswanathan et al. |
| 2005/0177150 A1 | 8/2005 | Amoah et al. |
| 2012/0098351 A1* | 4/2012 | Ross ................. A61B 18/1233 307/104 |
| 2014/0052126 A1 | 2/2014 | Long et al. |
| 2016/0022349 A1 | 1/2016 | Woloszko et al. |
| 2016/0058493 A1 | 3/2016 | Neal et al. |

FOREIGN PATENT DOCUMENTS

| | | |
|---|---|---|
| WO | WO2015/171921 A2 | 11/2015 |
| WO | WO2019/133606 A1 | 7/2019 |

* cited by examiner

SIGNAL GENERATORS FOR USE WITH TISSUE MODIFICATION SYSTEMS

PRIORITY CLAIM

This application claims priority to U.S. Provisional Patent Application No. 63/077,022, filed Sep. 11, 2020, which is incorporated herein by reference.

FIELD OF TECHNOLOGY

Certain embodiments of the present technology relate to signal generators for use in a treatment system, such as a tissue modification system, and to treatment systems that include a signal generator. Certain embodiments of the present technology also relate to methods for use by signal generators and/or by treatment systems that include a signal generator.

BACKGROUND

Pulsed electric field therapy can be used to deliver high voltage, short duration pulses to affect diseased tissue in a variety of endoluminal structures (airways, gastrointestinal tract), unresectable tissue targets (liver, pancreas, lungs, kidneys), or cancerous solid tumors. Signal generators are often used to generate the pulsed electric field signals that are used for such tissue treatment therapy. Because of the short duration of the pulses that are used to deliver the therapy, the signal generators often include switching networks that comprise solid state electronics. Signal generators may use their switching networks to generate biphasic treatment signals that include both positive and negative going pulses. Alternatively, signal generators may use their switching networks to generate monophasic pulses. Due to the high voltages and high currents that may exist under low impedance conditions, the solid state switches of a signal generator may on occasion fail and are a reliability concern.

SUMMARY

A signal generator, according to an embodiment of the present technology, includes one or more capacitors coupled between a high voltage rail and a low voltage rail and configured to store energy that can be used to selectively generate a treatment signal. The signal generator also includes a waveform shaping circuit, a controller, a voltage sense circuit, a current sense circuit, and a controller. The waveform shaping circuit is coupled to the one or more capacitors and includes first, second, third, and fourth switches, each of the switches configured to be selectively turned ON and OFF, and each of the switches configured to allow current to pass through the switch when the switch is turned ON and to prevent current from passing through the switch when the switch is turned OFF. The controller is configured to selectively control the switches to selectively turn a first pair of the switches ON and a second pair of the switches OFF during a first period of time, and selectively turn the first pair of the switches OFF and the second pair of the switches ON during a second period of time, in order to generate the treatment signal. The voltage sense circuit is configured to sense a voltage stored on the one or more capacitors. The current sense circuit is configured to sense current having a magnitude that is indicative of a magnitude of current flowing through a pair of the switches that are turned ON by the controller.

In accordance with certain embodiments, the controller is further configured to: selectively perform a first fault test on the signal generator, wherein during the first fault test the first pair of the switches are turned ON and the second pair of the switches are turned OFF; determine that the signal generator passed the first fault test in response to both the voltage sensed by the voltage sense circuit being below a specified voltage threshold, and a magnitude of the current sensed by the current sense circuit being above a specified current threshold; and determine that the signal generator failed the first fault test in response to the magnitude of the current sensed by the current sense circuit being below the specified current threshold.

In accordance with certain embodiments, as part of the first fault test the controller is configured to: determine that at least one of the switches within the first pair of the switches is stuck OFF, in response to the magnitude of the current sensed by the current sense circuit being below the specified current threshold, and the voltage sensed by the voltage sense circuit being above the specified voltage threshold; and determine that at least one of the switches within the second pair of the switches is stuck ON, in response to the magnitude of the current sensed by the current sense circuit being below the specified current threshold, and the voltage sensed by the voltage sense circuit being below the specified voltage threshold.

In accordance with certain embodiments, the controller is further configured to: selectively perform a second fault test on the signal generator, wherein during the second fault test the first pair of the switches are turned OFF and the second pair of the switches are turned ON; and determine that the signal generator passed the second fault test in response to both the voltage sensed by the voltage sense circuit being below the specified voltage threshold, and the magnitude of the current sensed by the current sense circuit being above the specified current threshold; and determine that the signal generator failed the second fault test in response to the magnitude of the current sensed by the current sense circuit being below the specified current threshold.

In accordance with certain embodiments, as part of the second fault test the controller is configured to: determine that at least one of the switches within the second pair of the switches is stuck OFF, in response to the magnitude of the current sensed by the current sense circuit being below the specified current threshold, and the voltage sensed by the voltage sense circuit being above the specified voltage threshold; and determine that at least one of the switches within the first pair of the switches is stuck ON, in response to the magnitude of the current sensed by the current sense circuit being below the specified current threshold, and the voltage sensed by the voltage sense circuit being below the specified voltage threshold.

In accordance with certain embodiments, the controller is configured to perform at least one of the first and the second fault tests in response to the signal generator being powered on.

In accordance with certain embodiments, the controller is implemented by at least one of a processor or a field programmable gate array (FPGA).

In accordance with certain embodiments, the first and the second switches are connected in series within a first branch of the waveform shaping circuit, and the third and the fourth switches are connected in series within a second branch of the waveform shaping circuit, wherein the first and the second branches are parallel to one another. A first output node of the waveform shaping circuit is between the first and the second switches, a second output node of the waveform shaping circuit is between the third and the fourth switches, the first pair of the switches includes the first and fourth switches, and the second pair of the switches includes the second and third switches. In accordance with a specific such embodiments, the first switch is connected between the high voltage rail and the first output node; the second switch is connected between the first output node and the low voltage rail; the third switch is connected between the high voltage rail and the second output node. and the fourth switch is connected between the second output node and the low voltage rail.

In accordance with certain embodiments, the signal generator further comprises a transformer including first and second primary windings and a secondary winding, wherein the first and the second primary windings are parallel to one another and coupled between the first and the second output nodes of the waveform shaping circuit, and wherein the current sensed by the current sense circuit is generated in response to a voltage being induced in the secondary winding and used to produce the treatment signal that is applied to patient tissue.

Certain embodiments of the present technology are directed to a method for use by a signal generator that includes one or more capacitors configured to store energy that can be used to selectively generate a treatment signal, and a waveform shaping circuit coupled to the one or more capacitors and including first, second, third, and fourth switches, each of the switches configured to be selectively turned ON and OFF, and each of the switches configured to allow current to pass through the switch when the switch is turned ON and to prevent current from passing through the switch when the switch is turned OFF. The method comprises: performing a first fault test on the signal generator, wherein during the first fault test a first pair of the switches are turned ON and a second pair of the switches are turned OFF; sensing a first voltage stored on the one or more capacitors, as part of the first fault test; sensing a first current having a magnitude that is indicative of a magnitude of current flowing through the first pair of the switches that are turned ON, as part of the first fault test; and determining whether the signal generator passed the first fault test based on the first voltage stored on the one or more capacitors, and based on the first current having the magnitude that is indicative of the magnitude of current flowing through the first pair of the switches that are turned ON, which are sensed as part of the first fault test.

In accordance with certain embodiments, determining whether the signal generator passed the first fault test comprises: determining that the signal generator passed the first fault test in response to both the first voltage sensed as part of the first fault test being below a specified voltage threshold, and a magnitude of the first current sensed as part of the first fault test being above a specified current threshold.

In accordance with certain embodiments, determining whether the signal generator passed the first fault test comprises: determining that the signal generator failed the first fault test in response to the magnitude of the first current sensed by the current sense circuit being below the specified current threshold. In accordance with certain embodiment, determining that the signal generator failed the first fault test further comprises: determining that at least one of the switches within the first pair of the switches is stuck OFF, in response to the magnitude of the first current sensed as part of the first fault test being below the specified current threshold, and the first voltage sensed as part of the first fault test being above the specified voltage threshold; or determining that at least one of the switches within the second pair of the switches is stuck ON, in response to the magnitude of the first current sensed as part of the first fault test being below the specified current threshold, and the first voltage sensed as part of the first fault test being below the specified voltage threshold.

In accordance with certain embodiments, the method further comprises performing a second fault test on the signal generator, wherein during the second fault test the first pair of the switches are turned OFF and the second pair of the switches are turned ON; sensing a second voltage stored on the one or more capacitors, as part of the second fault test; sensing a second current having a magnitude that is indicative of a magnitude of current flowing through the second pair of the switches that are turned ON, as part of the second fault test; and determining whether the signal generator passed the second fault test based on the second voltage stored on the one or more capacitors, and based on the second current having the magnitude that is indicative of the magnitude of current flowing through the second pair of the switches that are turned ON, which are sensed as part of the second fault test.

In accordance with certain embodiments, determining whether the signal generator passed the second fault test comprises: determining that the signal generator passed the second fault test in response to both the second voltage sensed as part of the second fault test being below the specified voltage threshold, and the magnitude of the current sensed as part of the second fault test being above the specified current threshold.

In accordance with certain embodiments, determining whether the signal generator passed the second fault test comprises: determining that the signal generator failed the second fault test in response to the magnitude of the second current sensed as part of the second fault test being below the specified current threshold.

In accordance with certain embodiments, determining that the signal generator failed the second fault test further comprises: determining that at least one of the switches within the second pair of the switches is stuck OFF, in response to the magnitude of the second current sensed as part of the second fault test being below the specified current threshold, and the second voltage sensed by as part of the second fault test being above the specified voltage threshold; or determining that at least one of the switches within the first pair of the switches is stuck ON, in response to the magnitude of the second current sensed as part of the second fault test being below the specified current threshold, and the second voltage sensed as part of the second fault test being below the specified voltage threshold.

In accordance with certain embodiments, a signal generator includes one or more capacitors configured to store energy that can be used to selectively generate a treatment signal. The signal generator also includes a switching network including first, second, third, and fourth switches, the first and the second switches connected in series with one another and in parallel with the one or more capacitors, and the third and the fourth switches connected in series with one another and in parallel with the one or more capacitors. Each switch of the first, second, third, and fourth switches is configured to be selectively turned ON and OFF, configured to allow current to pass through the switch when the switch is turned ON, and configured to prevent current from passing through the switch when the switch is turned OFF. The signal generator also includes a controller configured to selectively control the switches to selectively turn the first and the fourth switches ON and the second and the third switches OFF during a first period of time, and selectively turn the first and the fourth switches OFF and the second and the third switches ON during a second period of time, in order to generate the treatment signal. Additionally, the signal generator includes a voltage sense circuit configured to sense a voltage stored on the one or more capacitors, and a current sense circuit configured to sense current having a magnitude that is indicative of a magnitude of current flowing through the ones of the switches that are turned ON by the controller.

In certain embodiments, the controller is further configured to selectively perform a first fault test on the signal generator, wherein during the first fault test the first and the fourth switches are turned ON and the second and the third the switches are turned OFF; determine that the signal generator passed the first fault test in response to both the voltage sensed by the voltage sense circuit being below a specified voltage threshold, and a magnitude of the current sensed by the current sense circuit being above a specified current threshold; and determine that the signal generator failed the first fault test in response to the magnitude of the current sensed by the current sense circuit being below the specified current threshold.

In certain embodiments, the controller is further configured to: selectively perform a second fault test on the signal generator, wherein during the second fault test the first and the fourth switches are turned OFF and the second and the third switches are turned ON; and determine that the signal generator passed the second fault test in response to both the voltage sensed by the voltage sense circuit being below the specified voltage threshold, and the magnitude of the current sensed by the current sense circuit being above the specified current threshold; and determine that the signal generator failed the second fault test in response to the magnitude of the current sensed by the current sense circuit being below the specified current threshold.

In accordance with certain embodiments, the signal generator also includes a first output node between the first and the second switches; a second output node between the third and the fourth switches; and a transformer including first and second primary windings and a secondary winding. In a certain such embodiment, the first and the second primary windings are parallel to one another and coupled between the first and the second output nodes. Further, the current sensed by the current sense circuit is generated in response to a voltage being induced in the secondary winding and used to produce the treatment signal that is applied to patient tissue.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

DETAILED DESCRIPTION

Figure 1A:
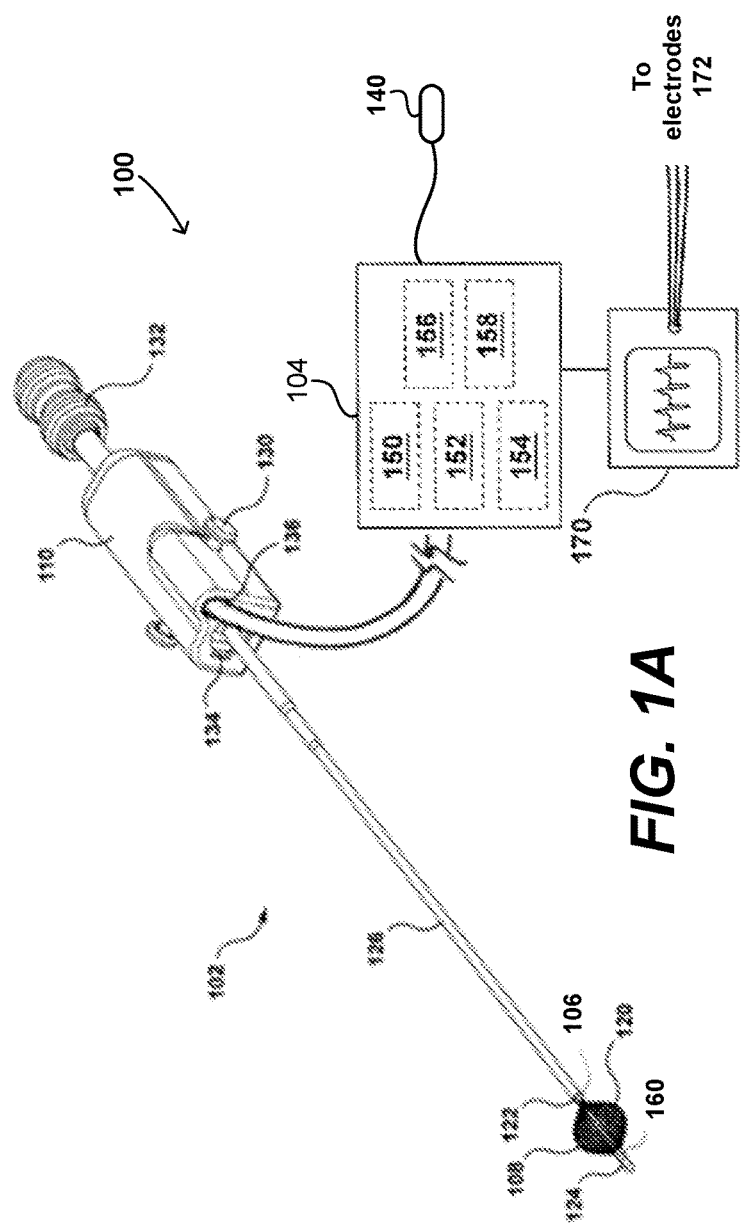
FIG. 1A illustrates an example treatment system used in treatment of a patient.
Figure 1B:
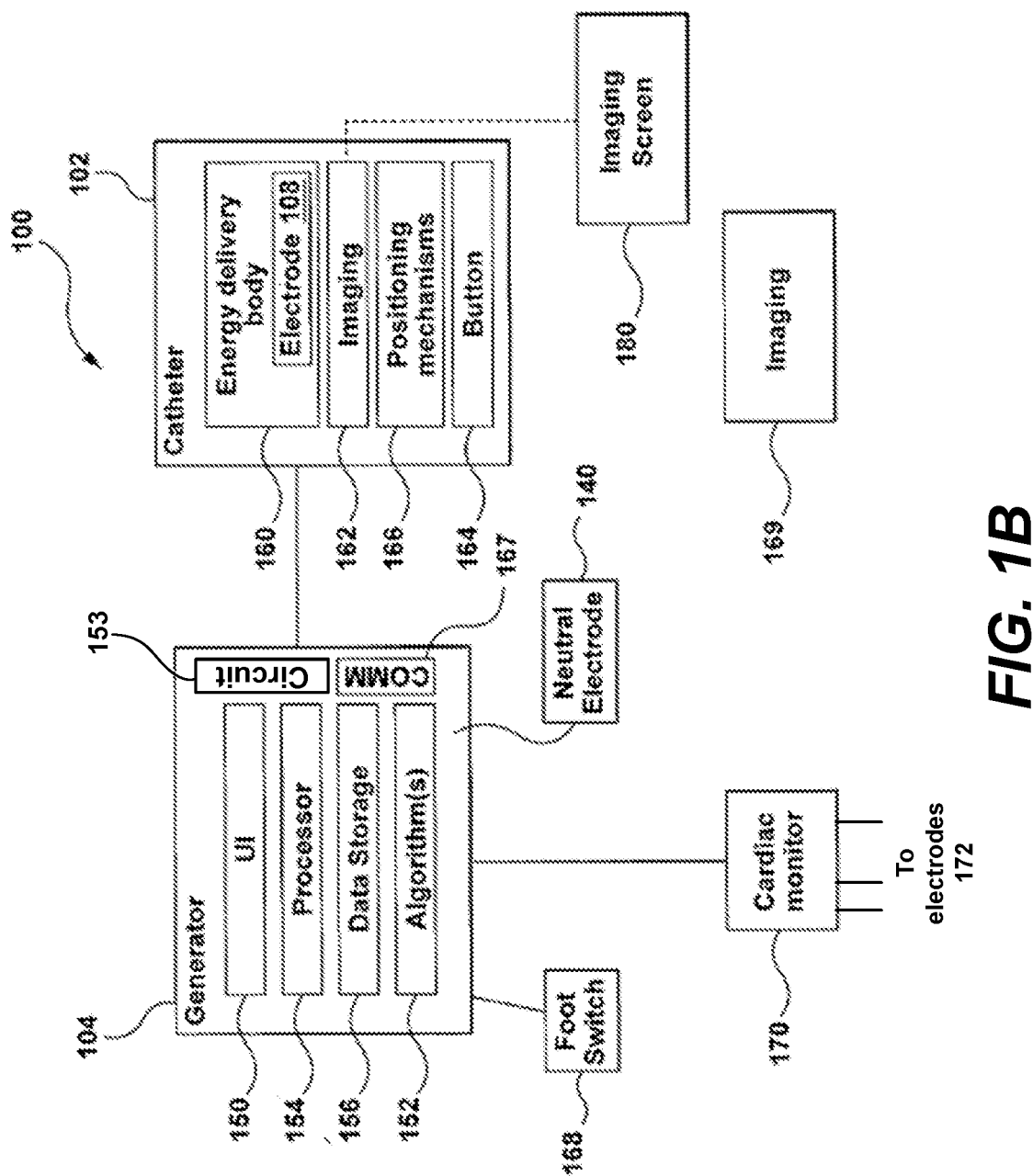
FIG. 1B is a schematic illustration of an embodiment of the treatment system, initially introduced in FIG. 1A.

Certain embodiments of the present relate to signal generators for use in a treatment system, such as a tissue modification system, but not limited thereto. FIG. 1A illustrates an example treatment system 100 used in treatment of a patient. FIG. 1B is a schematic illustration of the embodiment of the treatment system shown in FIG. 1A. In this embodiment, the system 100 comprises a therapeutic energy delivery instrument 102 (e.g., a catheter) connectable to a signal generator 104. The signal generator 104 can be referred to herein more succinctly as the generator 104. Referring to FIG. 1A, the instrument 102 is shown as having an elongate shaft 106 with at least one energy delivery body 108 near its distal end and a handle 110 at its proximal end. The instrument 102 is connectable to the generator 104 as part of a treatment system 100. Connection of the instrument 102 to the generator 104 provides electrical energy to the energy delivery body 108, among other features. In this embodiment, the energy delivery body 108 includes a plurality of wires or ribbons 120, constrained by a proximal end constraint 122 and a distal end constraint 124, and forms a spiral-shaped basket serving as an electrode. In an alternative embodiment, the wires or ribbons are straight instead of formed into a spiral-shape (i.e., configured to form a straight-shaped basket). In still another embodiment, the energy delivery body 108 is laser cut from a tube. It may be appreciated that a variety of other designs may be used. For example, an energy delivery body 108 can have a paddle shape and be comprised of a plurality of wires or ribbons arranged so as to form a flat pad or paddle. Such an energy delivery body 108 is flexible so as to be retracted into the shaft 106. Still referring to FIG. 1A, in this embodiment the energy delivery body 108 is self-expandable and delivered to a targeted area in a collapsed configuration. This collapsed configuration can be achieved, for example, by placing a sheath 126 over the energy delivery body 108. The instrument shaft 106 (within the sheath 126) terminates at the proximal end constraint 122, leaving the distal end constraint 124 essentially axially unconstrained and free to move relative to the shaft 106 of the instrument 102. Advancing the sheath 126 over the energy delivery body 108 allows the distal end constraint 124 to move forward, thereby lengthening/collapsing and constraining the energy delivery body 108. The energy delivery body 108 can also be referred to herein as the energy delivery electrode 108, the active electrode 108, or more succinctly as the electrode 108.

As shown in this example, the instrument 102 includes a handle 110 at its proximal end. In some embodiments, the handle 110 is removable, such as by pressing a handle removal button 130. In this embodiment, the handle 110 includes an energy delivery body manipulation knob or actuator 132 wherein movement of the actuator 132 causes expansion or retraction/collapse of the basket-shaped electrode. In this example, the handle 110 also includes a working port snap 134 for optional connection with an endoscope or other type of visualization device and a cable plug-in port 136 for connection with the generator 104. It may be appreciated that a variety of types of visualization may be used, including angiography (optionally including markers), computed tomography, optical coherence tomography, ultrasound, and direct video visualization, to name a few.

In this embodiment, the therapeutic energy delivery instrument 102 is connectable with the generator 104 along with a dispersive (return) electrode 140 applied externally to the skin of a patient. Thus, in this embodiment, monopolar energy delivery is achieved by supplying energy between the energy delivery body 108 disposed near the distal end of the instrument 102 and the return electrode 140. It will be appreciated, however, that bipolar energy delivery and other arrangements may alternatively be used. When using bipolar energy delivery, the therapeutic energy delivery instrument 102 may differ in overall design, such as to include a plurality of energy delivery bodies 108, or may appear similar in overall design, such as to include a single energy delivery body 108 which is configured to function in a bipolar manner. In some instances, bipolar energy delivery allows for the use of a lower voltage to achieve the treatment effect, as compared to monopolar energy delivery. In a bipolar configuration, the positive and negative poles are close enough together to provide a treatment effect both at the electrode poles and in-between the electrode poles. This can spread the treatment effect over a larger, shallower surface area thus requiring a lower voltage to achieve the treatment effect, compared to monopolar. Likewise, this lower voltage may be used to reduce the depth of penetration. In addition, lower voltage requirements may obviate the use of cardiac synchronization in particular cases if the delivered voltage is low enough to avoid stimulation of the cardiac muscle cells.

In this embodiment, the generator 104 includes a user interface 150, one or more energy delivery algorithms 152, a processor 154, a data storage/retrieval unit 156 (such as a memory and/or database), and an energy-storage and output sub-system 158 which generates and stores the energy to be delivered, and produces the desired waveform of the energy to be delivered. In some embodiments, one or more capacitors are used for energy storage/delivery, however any other suitable energy storage element may be used. In some embodiments, various switches are used to generate the desired waveform of the energy to be delivered. The energy-storage and output sub-system 158 can also be referred to as the output signal generator circuit 158, or more succinctly as the circuit 158. In addition, one or more communication ports 167 can be included.

In some embodiments, the generator 104 includes three sub-systems: 1) a high-energy storage system, 2) a high-voltage, medium-frequency switching amplifier, and 3) the system controller, firmware, and user interface. The system controller includes a cardiac synchronization trigger monitor that allows for synchronizing the pulsed energy output to the patient's cardiac rhythm. The generator takes in alternating current (AC) mains to power multiple direct current (DC) power supplies. The generator's controller can cause the DC power supplies to charge a high-energy capacitor storage bank before energy delivery is initiated. At the initiation of therapeutic energy delivery, the generator's controller, high-energy storage banks and a bi-phasic pulse amplifier can operate simultaneously to create a high-voltage, medium frequency output.

It will be appreciated that a multitude of generator electrical architectures may be employed to execute the energy delivery algorithms. In particular, in some embodiments, advanced switching systems are used which are capable of directing the pulsed electric field circuit to the energy delivering electrodes separately from the same energy storage and high voltage delivery system. Further, generators employed in advanced energy delivery algorithms employing rapidly varying pulse parameters (e.g., voltage, frequency, etc.) or multiple energy delivery electrodes may utilize modular energy storage and/or high voltage systems, facilitating highly customizable waveform and geographical pulse delivery paradigms. It should further be appreciated that the electrical architecture described herein above is for example only, and systems delivering pulsed electric fields may or may not include additional switching amplifier components.

The user interface 150 can include a touch screen and/or more traditional buttons to allow for the operator to enter patient data, select a treatment algorithm (e.g., energy delivery algorithm 152), initiate energy delivery, view records stored on the storage/retrieval unit 156, and/or otherwise communicate with the generator 104. The user interface 150 can include a voice-activated mechanism to enter patient data or may be able to communicate with additional equipment in the suite so that control of the generator 104 is through a secondary separate user interface.

In some embodiments, the user interface 150 is configured to receive operator-defined inputs. The operator-defined inputs can include a duration of energy delivery, one or more other timing aspects of the energy delivery pulse, power, and/or mode of operation, or a combination thereof. Example modes of operation can include (but are not limited to): system initiation and self-test, operator input, algorithm selection, pre-treatment system status and feedback, energy delivery, post energy delivery display or feedback, treatment data review and/or download, software update, or any combination or subcombination thereof. In accordance with certain embodiments, the user interface 150 displays information to a physician or technician, or some other user, during automated therapy delivery where all of the aforementioned dosage parameters (e.g., a duration of energy delivery, one or more other timing aspects of the energy delivery pulse, power, and/or mode of operation, or a combination thereof) can be preset. The user interface 150 can also be used to provide system status following one or more self-tests, and can provide a way for the user to acknowledge system status information.

In some embodiments, the system 100 also includes a mechanism for acquiring an electrocardiogram (ECG), such as an external cardiac monitor 170. Example cardiac monitors are available from AccuSync Medical Research Corporation. In some embodiments, the external cardiac monitor 170 is operatively connected to the generator 104. The cardiac monitor 170 can be used to continuously acquire an ECG signal. External electrodes 172 may be applied to the patient to acquire the ECG. The generator 104 analyzes one or more cardiac cycles and identifies the beginning of a time period during which it is safe to apply energy to the patient, thus providing the ability to synchronize energy delivery with the cardiac cycle. In some embodiments, this time period is within milliseconds of the R wave (of the ECG QRS complex) to avoid induction of an arrhythmia, which could occur if the energy pulse is delivered on a T wave. It will be appreciated that such cardiac synchronization is typically utilized when using monopolar energy delivery, however it may be utilized as part of other energy delivery methods.

In some embodiments, the processor 154, among other activities, modifies and/or switches between the energy-delivery algorithms, monitors the energy delivery and any sensor data, and reacts to monitored data via a feedback loop. In some embodiments, the processor 154 is configured to execute one or more algorithms for running a feedback control loop based on one or more measured system parameters (e.g., current), one or more measured tissue parameters (e.g., impedance), and/or a combination thereof.

The data storage/retrieval unit 156 stores data, such as related to the treatments delivered, and can optionally be downloaded by connecting a device (e.g., a laptop or thumb drive) to a communication port. In some embodiments, the device has local software used to direct the download of information, such as, for example, instructions stored on the data storage/retrieval unit 156 and executable by the processor 154. In some embodiments, the user interface 150 allows for the operator to select to download data to a device and/or system such as, but not limited to, a computer device, a tablet, a mobile device, a server, a workstation, a cloud computing apparatus/system, and/or the like. The communication ports, which can permit wired and/or wireless connectivity, can allow for data download, as just described but also for data upload such as uploading a custom algorithm or providing a software update.

The data storage/retrieval unit 156 can be, for example, a random access memory (RAM), a memory buffer, a hard drive, a database, an erasable programmable read-only memory (EPROM), an electrically erasable read-only memory (EEPROM), a read-only memory (ROM), flash memory, and/or so forth. The data storage/retrieval unit 156 can store instructions to cause the processor 154 to execute modules, processes and/or functions associated with the system 100.

Some embodiments the data storage/retrieval unit 156 comprises a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) can be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as ASICs, Programmable Logic Devices (PLDs), Read-Only Memory (ROM) and Random-Access Memory (RAM) devices. Other embodiments described herein relate to a computer program product, which can include, for example, the instructions and/or computer code discussed herein.

Examples of computer code include, but are not limited to, micro-code or micro-instructions, machine instructions, such as produced by a compiler, code used to produce a web service, and files containing higher-level instructions that are executed by a computer using an interpreter. For example, embodiments can be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

In some embodiments, the system 100 can be communicably coupled to a network, which can be any type of network such as, for example, a local area network (LAN), a wide area network (WAN), a virtual network, a telecommunications network, a data network, and/or the Internet, implemented as a wired network and/or a wireless network. In some embodiments, any or all communications can be secured using any suitable type and/or method of secure communication (e.g., secure sockets layer (SSL)) and/or encryption. In other embodiments, any or all communications can be unsecured.

FIG. 1B is a schematic illustration of an embodiment of the treatment system 100, initially introduced in FIG. 1A. In this embodiment, a dispersive (neutral) or return electrode 140 is operatively connected to the generator 104 while affixed to the patient's skin to provide a return path for the energy delivered via the instrument 102. The energy-delivery instrument 102 includes one or more energy delivery bodies 108 (comprised of electrode(s)), one or more sensors 160, one or more imaging modalities 162, one or more buttons 164, and/or positioning mechanisms 166 (e.g., such as, but not limited to, levers and/or dials on a handle with pull wires, telescoping tubes, a sheath, and/or the like) the one or more energy delivery bodies 108 into contact with the tissue. In some embodiments, a foot switch 168 is operatively connected to the generator 104 and used to initiate energy delivery. The dispersive electrode 140 can also be referred to herein as the neutral electrode 140, the return electrode 140, or more succinctly as the electrode 140.

As mentioned previously, the user interface 150 can include a touch screen and/or more traditional buttons to allow for the operator to enter patient data, select a treatment algorithm 152, initiate energy delivery, view records stored on the storage/retrieval unit 156, or otherwise communicate with the generator 104. The processor 154 manages and executes the energy-delivery algorithm, monitors the energy delivery and any sensor data, and reacts to monitored data via a feedback loop. The data storage/retrieval unit 156 stores data related to the treatments delivered and can be downloaded by connecting a device (e.g., a laptop or thumb drive) to a communication port 167.

The instrument 102 is operatively connected to the generator 104 and/or a separate imaging screen 180. Imaging modalities 162 can be incorporated into the instrument 102 or used alongside or in conjunction with the instrument 102. Alternatively or in addition, a separate imaging modality or apparatus 169 can be used, such as a commercially-available system (e.g., a bronchoscope). The separate imaging apparatus 169 can be mechanically, operatively, and/or communicatively coupled to the instrument 102 using any suitable mechanism.

Figure 2A:
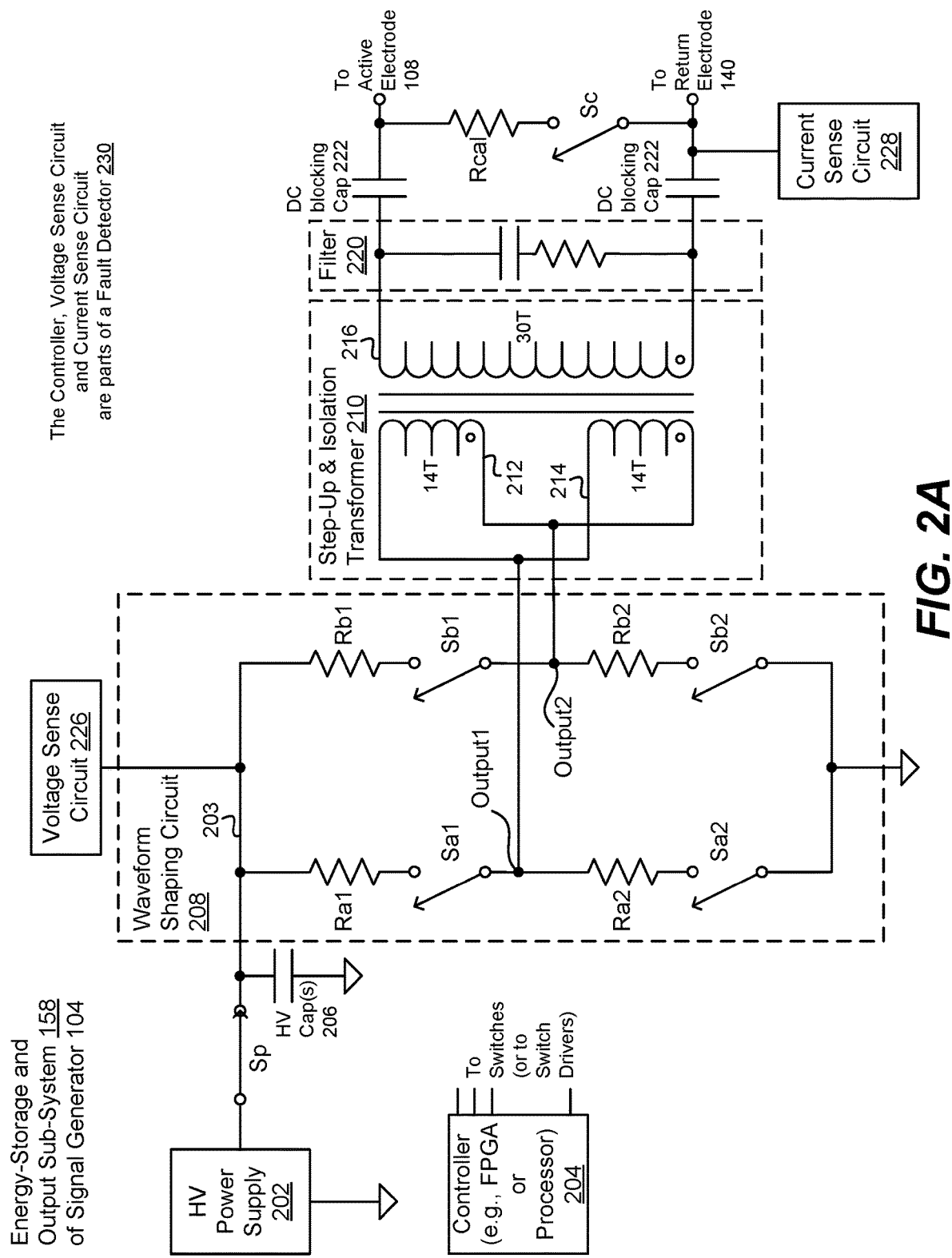
FIG. 2A is a circuit diagram of an output signal generator circuit, of a signal generator introduced in FIGS. 1A and 1B, according to an embodiment of the present technology.

FIG. 2A is a circuit diagram of the output signal generator circuit 158, of the signal generator 104, according to an embodiment of the present technology. Referring to FIG. 2A, the circuit 158 is shown as including a high voltage (HV) power supply 202, a controller 204, HV capacitor(s) 206, a waveform shaping circuit 208, a transformer 210, a filter 220, DC blocking capacitors 222, a voltage sense circuit 226, a current sense circuit 228, and a calibration resistor Rcal. The voltage sense circuit 226 and the current sense circuit 228 are part of a fault detector 230, which will be described in additional detail below. The circuit 158 can include additional circuitry, which is not shown, as would be appreciated by one of ordinary skill in the art.

The HV power supply 202 is configured to selectively provide a high voltage DC signal that is used to charge up the HV capacitor(s) 206 to a desired voltage level. In certain embodiments, the voltage sense circuit 226 can be used to determine when the HV capacitor(s) 206 are charged to the desired voltage level, but that need not be the case. The HV power supply 202 can include, e.g., an AC/DC converter that takes in alternating current (AC) maintains and outputs a direct current (DC) signal. The HV power supply 202 can also include step-up or step-down voltage regulator that receives the output of the AC/DC converter and converts the output of the AC/DC converter to a desired voltage level and mains the voltage level at the desired level. The HV power supply 202 can include additional and/or alternative circuitry, as would be appreciated by one of ordinary skill in the art. The switch Sp is used to selectively connect the HV power supply 202 to the HV capacitor(s) 206. Instead of (or in addition to) using the switch Sp to control whether the HV power supply 202 will charge the HV capacitor(s) 206, the output of the HV power supply 202 can be selectively enabled and disabled by the controller 204 to thereby selectively control whether at any given time the HV capacitor(s) 206 will be charged by the HV power supply 202. Accordingly, where the output of the HV power supply 202 can be selectively enabled and disabled by the controller 204, the switch Sp can optionally be eliminated.

The HV capacitor(s) 206 include one or more HV capacitors that are used to store the energy that is used to generate the treatment signal that is delivered to a patient via the electrodes 108 and 140, or some other electrodes. The HV capacitor(s) 206 are likely implemented using a bank of capacitors connected in series and/or in parallel with one another, depending on the specific implementation.

The waveform shaping circuit 208 is shown as including current limiting resistors Ra1, Ra2, Rb1, and Rb2, and switches Sa1, Sa2, Sb1, and Sb2. The switches are controlled by the controller 204, which can be implemented by a processor (e.g., 154 in FIGS. 1A and 1B), FPGA, or the like. In accordance with certain embodiments, each of the switches Sa1, Sa2, Sb1, and Sb2 is implemented using a respective insulated-gate bipolar transistor (IGBT). Where each of the switches is implemented using a respective IGBT, each of the switches can include or be associated with a respective IGBT driver (not shown), as would be appreciated by one of ordinary skill in the art. Each such IGBT driver can selectively turn ON (i.e., close) or turn OFF (i.e., open) a respective IGBT type switch responsive to a signal received from the controller 204. Output nodes of the waveform shaping circuit 208, which nodes are labeled Output 1 and Output 2, are connected to a transformer 210.

The transformer 210 is used to step up the voltage signal generated between the output nodes (Output 1 and Output 2) of the waveform shaping circuit 208 to a desired level. The transformer 210 is also used to isolate the HV power supply 202 and waveform shaping circuit 208 from the electrodes 108 and 140. In FIG. 2A, the primary side of the transformer is shown as including two parallel windings 212, 214, and the secondary side of the transformer is shown as including a single winding 216. In the embodiment shown, each of the primary windings 212, 214 has 14 turns, and the secondary winding 216 has 30 turns, which means the transformer is ~1:2 step-up transformer. However, it would also be possible for the primary and secondary windings to have different numbers of turns that provide for a different step-up (or step-down) ratios.

Turning a switch ON, as the phrase is used herein, does not mean that the switch is necessarily actually turned ON, as it is possible that the switch is stuck in an OFF position, and thus, is not responsive to being turned ON. Similarly, turning a switch OFF, as the phrase is used herein, does not mean that the switch is necessarily actually turned OFF, as it is possible that the switch is stuck in the ON position, and thus, is not responsive to being turned OFF. As will be described in more detail below, in accordance with certain embodiments of the present technology, fault tests described herein can be used to determine whether a switch is stuck ON or stuck OFF.

The filter 220, which is shown as being an RC snubber circuit including a resistor and capacitor connected in series, is used to filter out high-frequency transients or ringing that may be caused by leakage inductance of the transformer 210. The DC blocking capacitors 222 are used to prevent dangerous low frequency or DC currents from flowing through patient tissue. The calibration resistor Rcal, which has a known (i.e., predetermined) resistance with a very tight tolerance, can be used during a self-test to verify that the voltage sense circuit 226 and the current sense circuit 228 are operating properly by measuring the voltage and current through the known resistance (i.e., Rcal). The switch Sc is used to switch the calibration resistor Rcal into and out of the circuit shown in FIG. 2A.

Figure 3:
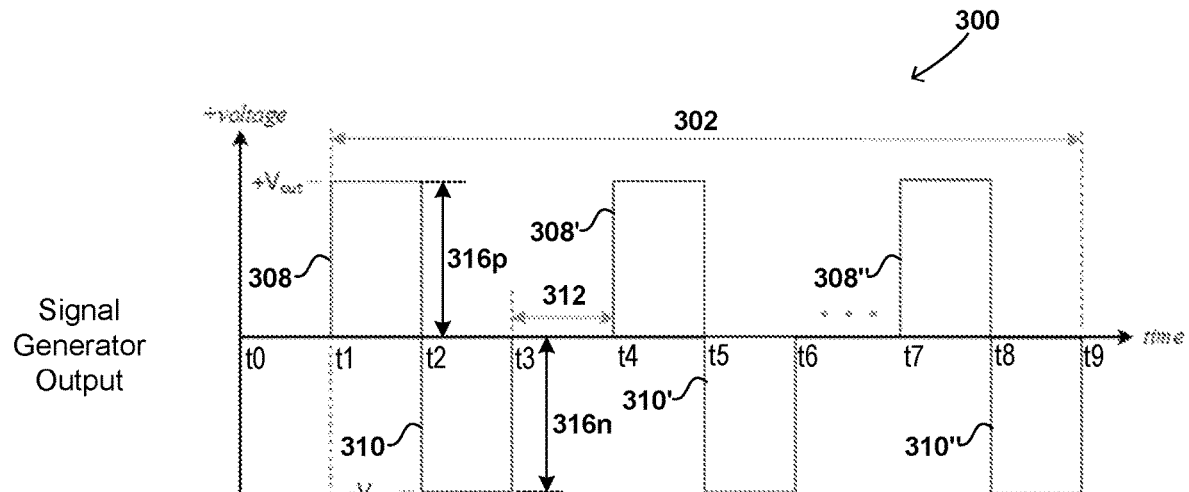
FIG. 3 illustrates an embodiment of a waveform of a biphasic treatment signal prescribed by an energy delivery algorithm.

FIG. 3 illustrates an embodiment of a waveform 300 of a treatment signal prescribed by an energy delivery algorithm 152. The waveform 300 can also be referred to as a biphasic treatment signal 300, or more succinctly as a treatment signal 300. In FIG. 3, one packet 302 is shown. However, the waveform 300 can also include one or more additional packets (not shown), wherein pairs of packets are separated by one another by a rest period. In this embodiment, the packet 302 is comprised of a first biphasic cycle (comprising a first positive pulse peak 308 and a first negative pulse peak 310), a second biphasic cycle (comprising a second positive pulse peak 308' and a second negative pulse peak 310'), and an nth biphasic cycle (comprising an nth positive pulse peak 308" and an nth negative pulse peak 310"), where n is an integer that is greater than or equal to 3. The first and second biphasic pulses are separated by dead time 312 (i.e., a pause) between each pulse. In this embodiment, the biphasic pulses are symmetric so that the set voltage 316p for the positive peaks is the same as the set voltage 316n for the negative peaks, however that need not be the case. Here, the biphasic, symmetric waves are also square waves such that the magnitude and time of the positive voltage wave is approximately equal to the magnitude and time of the negative voltage wave, however that need not be the case.

When using a bipolar configuration to apply a treatment signal, portions of cells (e.g., airway wall cells) facing the negative voltage wave undergo cellular depolarization in these regions, where a normally negatively charged cell membrane region briefly turns positive. Conversely, portions of the cells facing the positive voltage wave undergo hyperpolarization in which the cell membrane region's electric potential becomes extremely negative. When used to treat airway walls of a patient's lungs, it may be appreciated that in each positive or negative phase of the biphasic pulse, portions of the airway wall cells will experience the opposite effects. For example, portions of cell membranes facing the negative voltage will experience depolarization, while the portions 180° to this portion will experience hyperpolarization. In some embodiments, the hyperpolarized portion faces the dispersive or return electrode 140.

The voltages used and considered may be the tops of square-waveforms, may be the peaks in sinusoidal or sawtooth waveforms, or may be the RMS voltage of sinusoidal or sawtooth waveforms. In some embodiments, the energy is delivered in a monopolar fashion and each high voltage pulse or the set voltage 316 is between about 500 V to 10,000 V, particularly about 500 V to 5000 V, about 500 V to 4000 V, about 1000 V to 4000 V, about 2500 V to 4000V, about 2000 to 3500, about 2000 V to 2500V, about 2500 V to 3500 V, including all values and subranges in between including about 500 V, 1000 V, 1500 V, 2000 V, 2500 V, 3000 V, 3500 V, 4000 V. In some embodiments, each high voltage pulse is in range of approximately 1000 V to 2500 V which can penetrate the airway wall W in particular parameter combinations so as to treat or affect particular cells somewhat shallowly, such as epithelial cells. In some embodiments, each high voltage pulse is in the range of approximately 2500 V to 4000 V which can penetrate the airway W in particular parameter combinations so as to treat or affect particular cells somewhat deeply positioned, such as submucosal cells or smooth muscle cells.

It may be appreciated that the set voltages 316p, 316n may vary depending on the specific implementation. In bipolar delivery, a lower voltage may be used due to the smaller, more directed electric field. In some embodiments, the energy is delivered in a bipolar fashion and each pulse is in the range of approximately 100 V to 1900 V, particularly 100 V to 999 V, more particularly approximately 500 V to 800 V, such as 500 V, 550 V, 600 V, 650 V, 700 V, 750 V, 800 V. In other embodiments, the energy is delivered in a bipolar fashion and each pulse is between approximately 50 and 5000 volts, including 250 to 1500 volts.

The bipolar voltage selected for use in therapy is dependent on the separation distance of the electrodes, whereas with monopolar electrode configurations that use a distant dispersive pad electrode may be delivered with less consideration for exact placement of the catheter electrode and dispersive electrode placed on the body. In monopolar electrode embodiments, larger voltages are typically used due to the dispersive behavior of the delivered energy through the body to reach the dispersive electrode, on the order of 10 cm to 100 cm effective separation distance. Conversely, in bipolar electrode configurations, the relatively close active regions of the electrodes, on the order of 0.5 mm to 10 cm, including 1 mm to 1 cm, results in a greater influence on electrical energy concentration and effective dose delivered to the tissue from the separation distance. For instance, if the targeted voltage-to-distance ratio is 3000 V/cm to evoke the desired clinical effect at the appropriate tissue depth (1-3 mm), if the separation distance is changed from 1 mm to 1.2 mm, this would result in a necessary increase in treatment voltage from 300 to about 360 V, a change of 20%.

The number of biphasic cycles per second of time is the frequency. In some embodiments, biphasic pulses are utilized to reduce undesired muscle stimulation, particularly cardiac muscle stimulation. In other embodiments, the pulse waveform is monophasic, and there is no clear inherent frequency, and instead a fundamental frequency may be considered by doubling the monophasic pulse length to derive the frequency. In some embodiments, the signal has a frequency in the range 100 kHz-1 MHz, more particularly 100 kHz-1000 kHz. In some embodiments, the signal has a frequency in the range of approximately 100-600 kHz which typically penetrates the airway so as to treat or affect particular cells somewhat deeply positioned, such as submucosal cells or smooth muscle cells. In some embodiments, the signal has a frequency in range of approximately 600 kHz-1000 kHz or 600 kHz-1 MHz which typically penetrates the airway wall W so as to treat or affect particular cells somewhat shallowly, such as epithelial cells. It may be appreciated that at some voltages, frequencies at or below 300 kHz may cause undesired muscle stimulation. Therefore, in some embodiments, the signal has a frequency in the range of 400-800 kHz or 500-800 kHz, such as 500 kHz, 550 kHz, 600 kHz, 650 kHz, 700 kHz, 750 kHz, 800 kHz. In particular, in some embodiments, the signal has a frequency of 600 kHz. In addition, cardiac synchronization is typically utilized to reduce or avoid undesired cardiac muscle stimulation during sensitive rhythm periods. It may be appreciated that even higher frequencies may be used with components which minimize signal artifacts.

Figure 4:
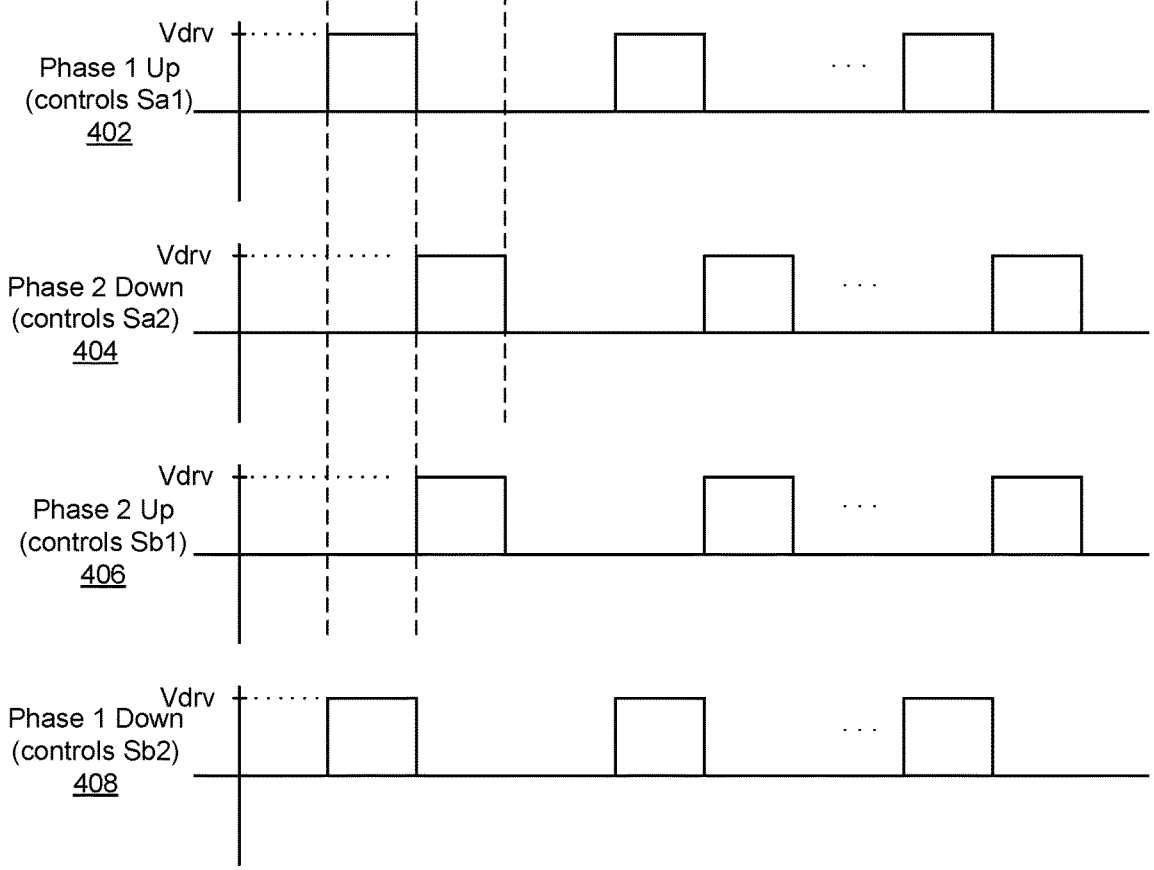
FIG. 4 illustrates signals generated by a controller of the circuit introduced in FIG. 2A and used to control switches to generate a biphasic treatment signal.

FIG. 4 illustrates signals generated by the controller 204 in FIG. 2A (e.g., the processor 154 in FIGS. 1A and 1B) to control the switches Sa1, Sa2, Sb1, and Sb2 to generate the biphasic treatment signal 300 shown in FIG. 3. The aforementioned switches collectively provide for a switching network. In FIG. 4, the phase 1 up signal 402 is used to control the switch Sa1, the phase 2 down signal is used to control the switch Sa2, the phase 2 up signal 406 is used to control the switch Sb1, and the phase 2 down signal 408 is used to control the switch Sb2. Referring to FIGS. 2A, 3, and 4, during the period of time between times t1 and t2, the phase 1 up signal 402 turns ON (i.e. closes) the switch Sa1 and the phase 1 down signal 408 turns ON (i.e., closes) the switch Sb2, and the phase 2 down signal 404 keeps the switch Sa2 turned OFF (i.e., open) and the phase 2 up signal 406 keeps the switch Sb1 turned OFF (i.e., open), which results in the first positive pulse peak 308 shown in FIG. 3.

During the period of time between times t2 and t3, the phase 1 up signal 402 turns OFF (i.e. opens) the switch Sa1 and the phase 1 down signal 408 turns OFF (i.e., opens) the switch Sb2, and the phase 2 down signal 404 turns ON (i.e., closes) the switch Sa2 and the phase 2 up signal 406 turns ON (i.e., opens) the switch Sb1, which results in the first negative pulse peak 310 shown in FIG. 3. During the period of time between times t3 and t4, the phase 1 up signal 402 keeps the switch Sa1 turned OFF (i.e., open) and the phase 1 down signal 408 keeps the switch Sb2 turned OFF (i.e., open), and the phase 2 down signal 404 turns OFF (i.e., opens) the switch Sa2 and the phase 2 up signal 406 turns OFF (i.e., opens) the switch Sb1, which results in the dead time 312 that follows first negative pulse peak 310 shown in FIG. 3. During the period of time between times t4 and t5, the phase 1 up signal 402 turns ON (i.e. closes) the switch Sa1 and the phase 1 down signal 408 turns ON (i.e., closes) the switch Sb2, and the phase 2 down signal 404 keeps the switch Sa2 turned OFF (i.e., open) and the phase 2 up signal 406 keeps the switch Sb1 turned OFF (i.e., open), which results in the second positive pulse peak 308' shown in FIG. 3. During the period of time between times t5 and t6, the phase 1 up signal 402 turns OFF (i.e. opens) the switch Sa1 and the phase 1 down signal 408 turns OFF (i.e., opens) the switch Sb2, and the phase 2 down signal 404 turns ON (i.e., closes) the switch Sa2 and the phase 2 up signal 406 turns ON (i.e., opens) the switch Sb1, which results in the second negative pulse peak 310' shown in FIG. 3. During the period of time between times t6 and t7, the phase 1 up signal 402 keeps the switch Sa1 turned OFF (i.e., open) and the phase 1 down signal 408 keeps the switch Sb2 turned OFF (i.e., open), and the phase 2 down signal 404 turns OFF (i.e., opens) the switch Sa2, and the phase 2 up signal 406 turns OFF (i.e., opens) the switch Sb1, which results in a further dead time that follows second negative pulse peak 310' shown in FIG. 3. Additional positive pulse peaks and negative pulse peaks (e.g., 308" and 310") and additional deadtimes can be produced in a similar manner, as desired.

As can be appreciated from the above discussion of FIGS. 2A, 3, and 4, in order for an appropriate treatment signal to be generated, such as the biphasic treatment signal 300 shown in FIG. 3, the various switches Sa1, Sa2, Sb1, and Sb2 of the signal generator 104 (and more specifically, the energy-storage and output sub-system 158) must operate properly. However, do to the high voltages that these switches are subjected to, they sometimes experience faults, which may cause one or more of the switches to become stuck ON (i.e., closed), and/or one or more switches to become stuck OFF (i.e., open). To identify such potential faults, the signal generator 104 may perform one or more fault tests to classify a fault status of the signal generator 104 to thereby ensure proper operation of the signal generator. Where the fault test identifies a fault, an error message can be generated, in response to which the signal generator 104 may be serviced (aka repaired) by an appropriate technician.

More specifically, in accordance with certain embodiments, the signal generator 104 includes a fault detector 230, which includes a voltage sense circuit 226 and a current sense circuit 228, shown in FIG. 2A. The fault detector 230 can also include the controller 204 (e.g., the processor 154, or an FPGA, or the like) that is used to control the switches Sa1, Sa2, Sb1, and Sb2, the voltage sense circuit 226, and the current sense circuit 228, during a fault test. Additionally, the controller 204 can obtain voltage measurements from the voltage sense circuit 226, and current measurements from the current sense circuit 228, during a fault test. A fault can be said to be detected if a fault test fails (i.e., is not passed). The controller 204 can also determine, based on such voltage and current measurements, whether a fault is detected, as will be described in additional detail below. The controller 204 can be configured to set the various switches to predetermined states (e.g., test states) to allow the fault status to be classified. Fault tests may be performed upon powering on the signal generator 104, such as for a Power on Self-Test (POST) and/or at predetermined intervals or in response to certain event that occur during use, such as just prior to tissue ablation energy delivery and/or capacitor discharge, but not limited thereto.

Figure 2B:
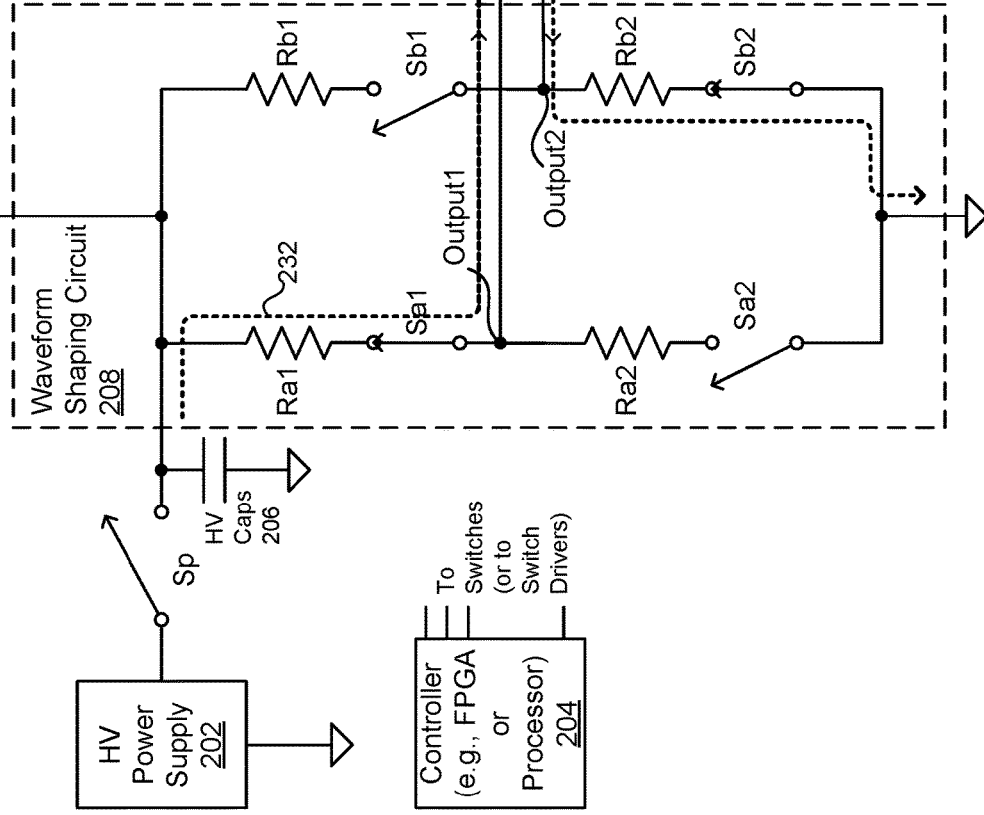
FIG. 2B, which includes the same circuit diagram introduced in FIG. 2A, is used to explain how a first fault test can be performed on a switching network of a signal generator, according to an embodiment of the present technology.
Figure 2B:
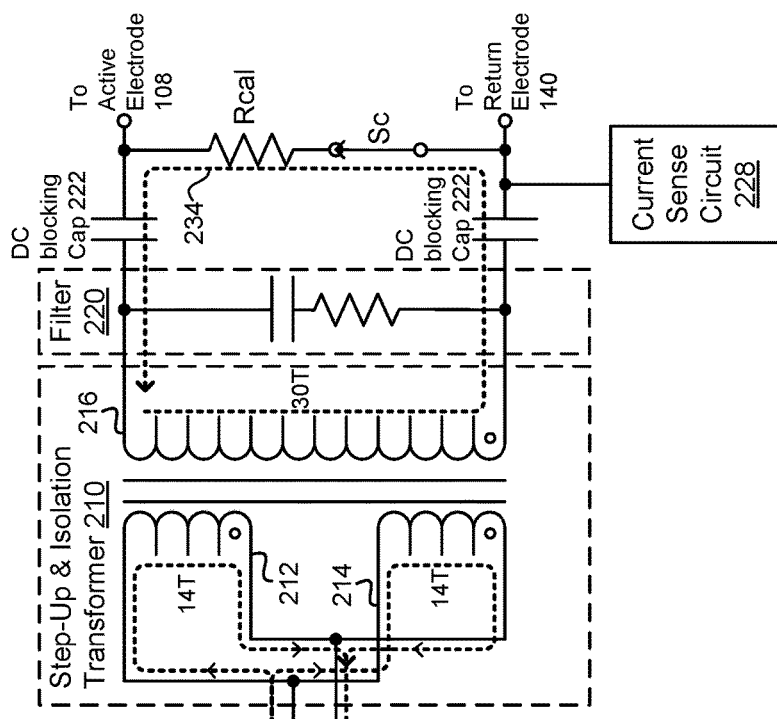

In accordance with certain embodiments, first and second fault tests are performed under the control of the controller 204, and prior to the first fault test, the HV capacitor(s) 206 is/are charged, e.g., by turning ON (i.e., closing) the switch Sp for a period of time, as shown in FIG. 2A, while the switches Sa1, Sa2, Sb1, and Sb2 are all turned OFF (i.e., opened), as also shown in FIG. 2A. The switch Sp is then turned OFF (i.e., opened) just prior to the initiation of the first fault test. During the first fault test, the switches Sa1 and Sb2 are turned ON (i.e., closed), the switches Sa2 and Sb1 are turned OFF (i.e., open), and the switch Sc is also turned ON (i.e., closed), as shown in FIG. 2B. Presuming the switches all operate properly, a current should flow along the path specified by the dotted line labeled 232 in FIG. 2B. As the current 232 flows through the primary windings 212, 214 of the transformer 210, a secondary current, which should flow along the path specified by the dotted line labeled 234 in FIG. 2B, is induced in the secondary winding 216 of the transformer 210. The secondary current 234 will cause a current to flow through the resistor Rcal, which current is sensed by the current sense circuit 228 as part of the first fault test. Additionally, as part of the first fault test a voltage is sensed by the voltage sense circuit 226 at a high voltage rail of the waveform shaping circuit 208. If the voltage sense circuit 226 senses a low voltage (i.e., a voltage below a specified voltage threshold), and the current sense circuit 228 senses a current (i.e., a current having a magnitude above a specified current threshold), then there is a determination that the signal generator 104 passed the first fault test. However, if the voltage sense circuit 226 senses a high voltage (i.e., a voltage above the specified voltage threshold), and/or the current sense circuit 228 senses no current (and more specifically, a current having a magnitude below the specified current threshold), then there is a determination that the signal generator 104 failed the first fault test. In certain embodiments, there is only a determination of whether or not the first fault test resulted in a pass or a fail. In other embodiments, the reason for first fault test failure can also be identified, which reason can be used by a technician, or the like, to repair the signal generator. Table 1, shown below, specifies the various types of faults that may result in a failure of the first fault test.

TABLE 1

| Voltage measured by Voltage Sense Circuit 226 | Current Measured by Current Sense Circuit 228 | Pass or Fail | Reason for Failure |
| --- | --- | --- | --- |
| Low Voltage | Current | Pass | N/A |
| High Voltage | No Current | Fail | Sa1 or Sb2 stuck OFF (i.e., open) |
| Low Voltage | No Current | Fail | Sa2 or Sb1 stuck ON (i.e., closed) |

Figure 2C:
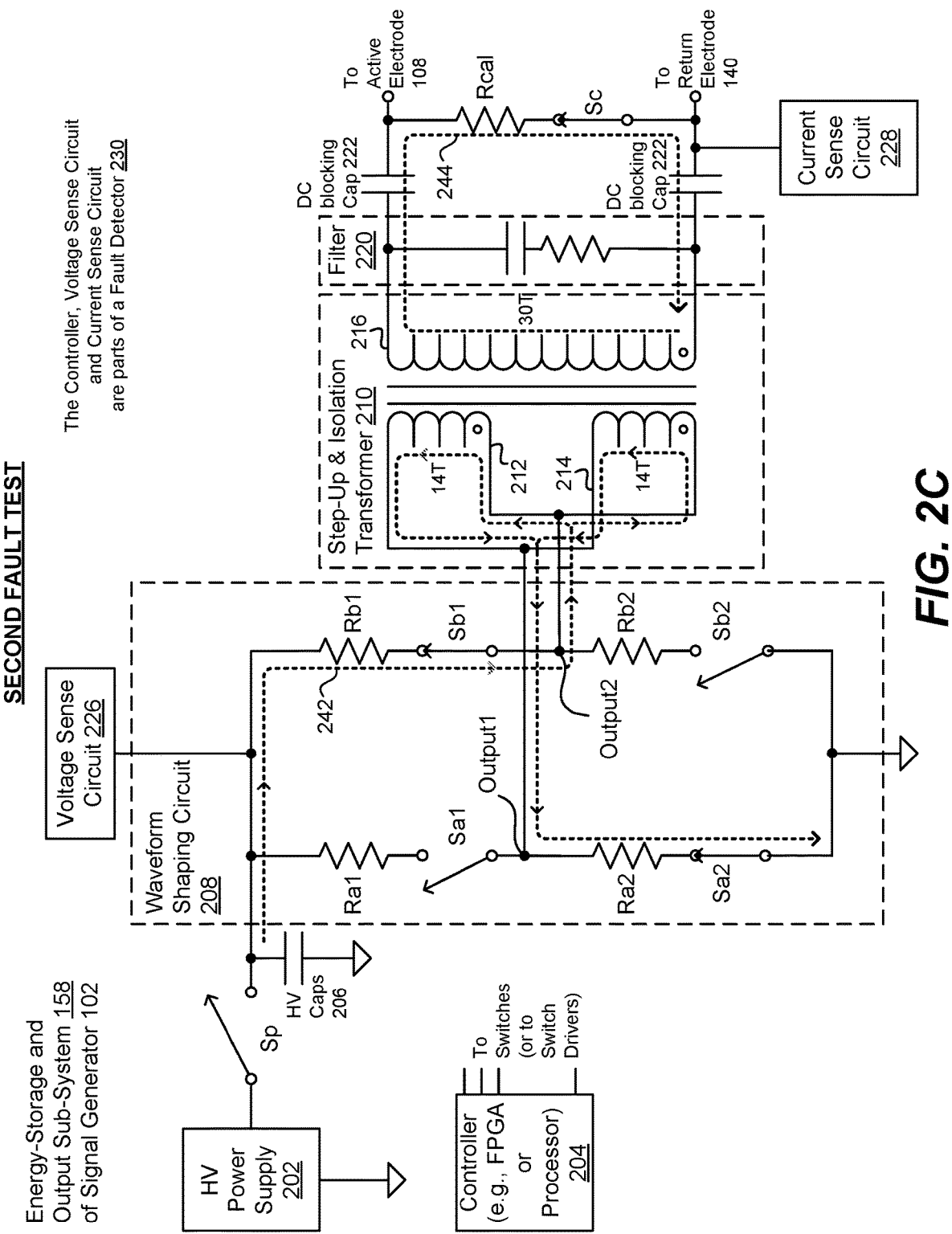
FIG. 2C, which includes the same circuit diagram introduced in FIG. 2A, is used to explain how a second fault test can be performed on a switching network of a signal generator, according to an embodiment of the present technology.

Prior to the second fault test, the HV capacitor(s) 206 is/are charged, e.g., by turning ON (i.e., closing) the switch Sp for a period of time, as shown in FIG. 2A, while the switches Sa1, Sa2, Sb1, and Sb2 are all turned OFF (i.e., opened), as also shown in FIG. 2A. The switch Sp is then turned OFF (i.e., opened) just prior to the initiation of the second fault test. During the second fault test, the switches Sa1 and Sb2 are turned OFF (i.e., open), the switches Sa2 and Sb1 are turned ON (i.e., closed), and the switch Sc is also turned ON (i.e., closed), as shown in FIG. 2C. Presuming the switches all operate properly, a current should flow along the path specified by the dotted line labeled 242 in FIG. 2C. As the current 242 flows through the primary windings 212, 214 of the transformer 210, a secondary current, which should flow along the path specified by the dotted line labeled 244 in FIG. 2C, is induced in the secondary winding 216 of the transformer 210. The secondary current 244 will cause a current to flow through the resistor Rcal, which current is sensed by the current sense circuit 228 as part of the second fault test. Additionally, as part of the second fault test a voltage is sensed by the voltage sense circuit 226 at the high voltage rail of the waveform shaping circuit 208. If the voltage sense circuit 226 senses a low voltage (i.e., a voltage below a specified voltage threshold), and the current sense circuit 228 senses a current (i.e., a current having a magnitude above a specified current threshold), then there is a determination that the signal generator 104 passed the first fault test. However, if the voltage sense circuit 226 senses a high voltage (i.e., a voltage above the specified voltage threshold), and/or the current sense circuit 228 senses no current (and more specifically, a current having a magnitude below the specified current threshold), then there is a determination that the signal generator 104 failed the second fault test. In certain embodiments, there is only a determination of whether or not the second fault test resulted in a pass or a fail. In other embodiments, the reason for second fault test failure can also be identified, which reason can be used by a technician, or the like, to repair the signal generator. Table 2, shown below, specifies the various types of faults that may result in a failure of the second fault test.

TABLE 2

| Voltage measured by Voltage Sense Circuit 226 | Current Measured by Current Sense Circuit 228 | Pass or Fail | Reason for Failure |
| --- | --- | --- | --- |
| Low Voltage | Current | Pass | N/A |
| High Voltage | No Current | Fail | Sa2 or Sb1 stuck OFF (i.e., open) |
| Low Voltage | No Current | Fail | Sa1 or Sb2 stuck ON (i.e., closed) |

In the first fault test, sensing the voltage on the high voltage rail is the same as sensing the voltage stored on the HV capacitor(s) 206. Similarly, in the second fault test, sensing the voltage on the high voltage rail is the same as sensing the voltage stored on the HV capacitor(s) 206. Further, since the first fault test fails if the sensed current is below the specified sense threshold, it is possible to detect a failed first fault test based solely on the sensed current, without taking into account a sensed voltage. Similarly, since the second fault test fails if the sensed current is below the specified sense threshold, it is possible to detect a failed second fault test based solely on the sensed current, without taking into account a sensed voltage.

Figure 5A:
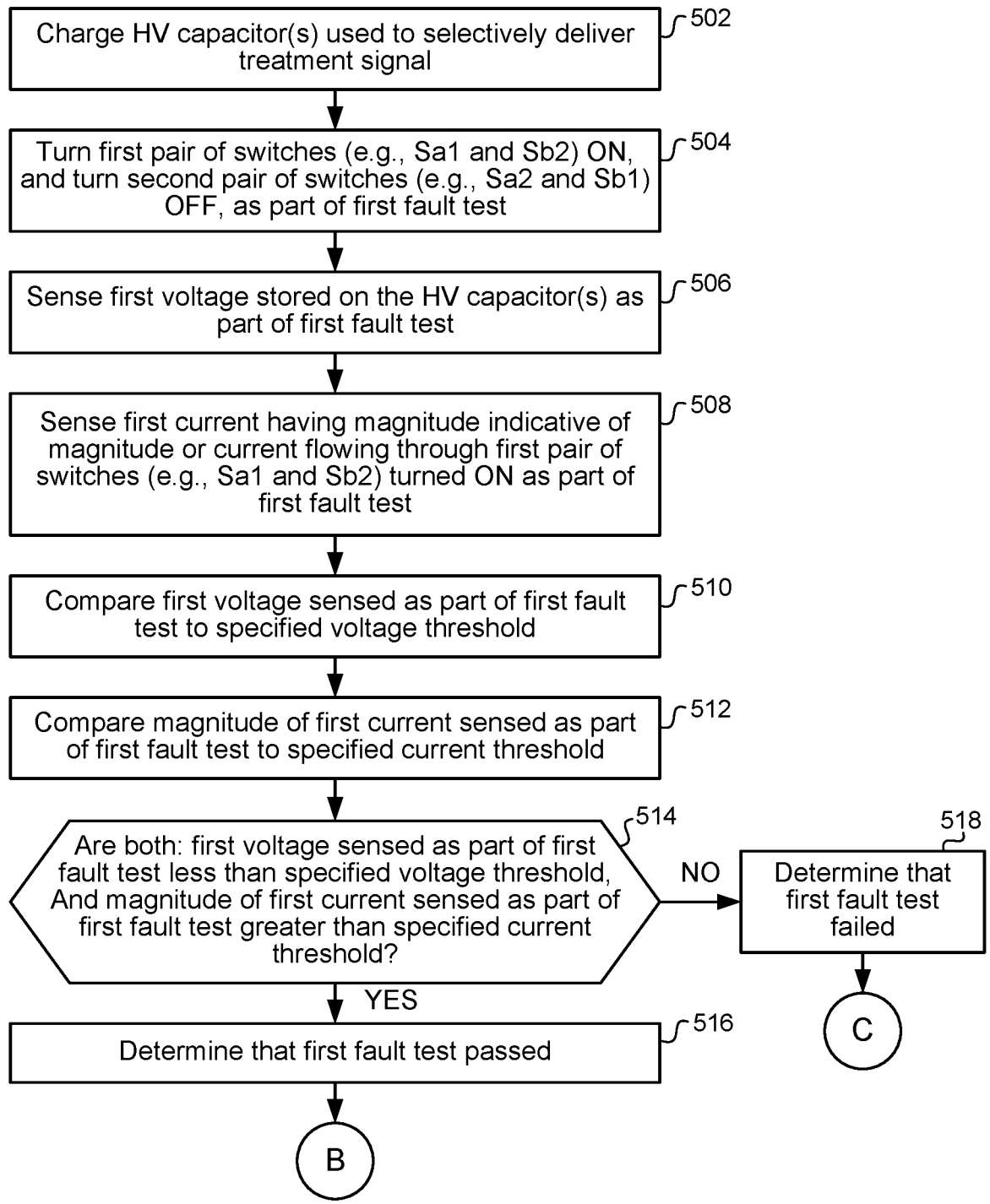
FIG. 5A is a high level flow diagram that is used to summarize a method for performing the first fault test that was introduced in FIG. 2B.

Reference is now made to FIG. 5A, which is a high level flow diagram that is used to summarize a method for performing the first fault test that was discussed above with reference to FIG. 2B. Referring to FIG. 5A, step 502 involves charging the HV capacitor(s) that is/are used to selectively deliver a treatment signal to patient tissue. Step 504 involves turning ON a first pair of switches (e.g., Sa1 and Sb2), and turning OFF a second pair of switches (e.g., Sa2 and Sb1). Steps 502 and 504 can be performed, e.g., by the controller 204. Step 502 can be considered to be separate from the first fault test, e.g., to occur prior to the first fault test being initiated.

Step 506 involves sensing a first voltage stored in the HV capacitor(s). Step 506 can be performed by the voltage sense circuit 226 under the control of the controller 204. Step 508 involves sensing a first current having a magnitude indicative of magnitude or current flowing through the first pair of switches (e.g., Sa1 and Sb2) that are turned ON as part of first fault test. Step 508 can be performed, e.g., by the current sense circuit 228 under the control of the controller 204. The order of steps 506 and 508 can be reversed, or steps 506 and 508 can be performed at the same time.

Step 510 involves comparing the first voltage sensed as part of first fault test to a specified voltage threshold. Step 512 involves comparing the magnitude of first current sensed as part of first fault test to a specified current threshold. The order of steps 510 and 512 can be reversed, or steps 510 and 512 can be performed at the same time.

At step 514 there is a determination of whether the first voltage sensed as part of first fault test is less than the specified voltage threshold, and whether the magnitude of first current sensed as part of first fault test greater than the specified current threshold. Step 514 can be broken into two or more steps.

If the answer to the determination at step 514 is Yes, then flow goes to step 516, and there is a determination that the first fault test passed. In other words, the first fault test is passed if both of the following conditions are true: the first voltage sensed as part of first fault test is less than the specified voltage threshold; and the magnitude of first current sensed as part of first fault test is greater than the specified current threshold. If the first fault test is passed, then the second fault test is performed. Details of a method for performing the second fault test are discussed below with reference to FIG. 5B.

If the answer to the determination at step 514 is No, then flow goes to step 518 and there is a determination that the first fault test failed. In other words, the first fault test is failed if at least one of the following conditions are not true: the first voltage sensed as part of first fault test is less than the specified voltage threshold; or the magnitude of first current sensed as part of first fault test is greater than the specified current threshold. If the first fault test is failed, then there can be a determination as to why the first fault test failed. Details of a method for determining why the first fault test failed are discussed below with reference to FIG. 5C.

Figure 5B:
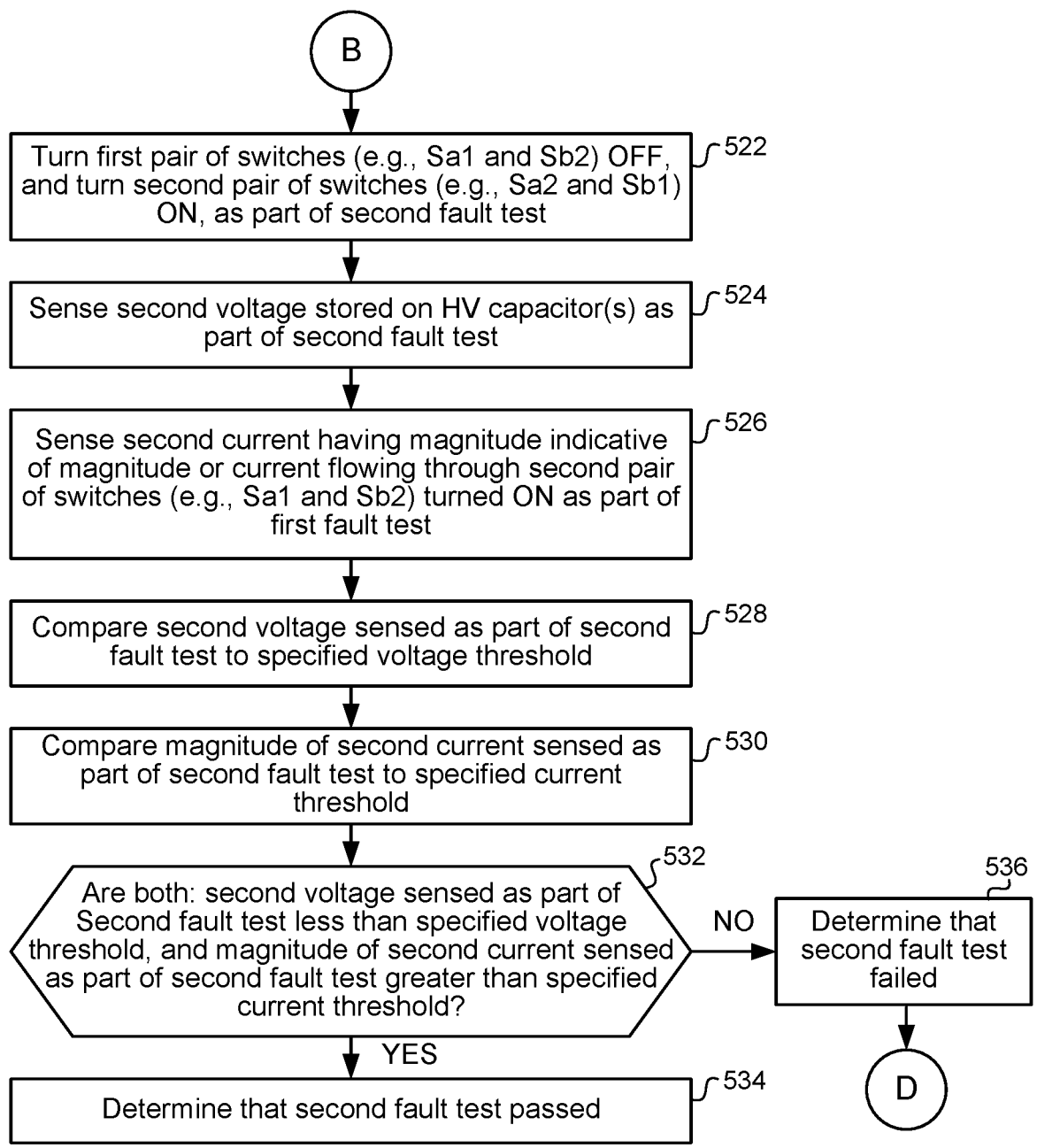
FIG. 5B is a high level flow diagram that is used to summarize a method for performing the second fault test that was introduced in FIG. 2C.

Reference is now made to FIG. 5B, which is a high level flow diagram that is used to summarize a method for performing the second fault test that was discussed above with reference to FIG. 2C. Referring to FIG. 5B, step 522 involves turning OFF the first pair of switches (e.g., Sa1 and Sb2), and turning ON the second pair of switches (e.g., Sa2 and Sb1). Step 522 can be performed, e.g., by the controller 204.

Step 524 involves sensing a second voltage stored in the HV capacitor(s). Step 524 can be performed by the voltage sense circuit 226 under the control of the controller 204. Step 526 involves sensing a second current having a magnitude indicative of magnitude or current flowing through the second pair of switches (e.g., Sa2 and Sb1) that are turned ON as part of second fault test. Step 526 can be performed, e.g., by the current sense circuit 228 under the control of the controller 204. The order of steps 524 and 526 can be reversed, or steps 524 and 526 can be performed at the same time.

Step 528 involves comparing the second voltage sensed as part of second fault test to a specified voltage threshold, which can be the same threshold referred to at step 510, but that need not be the case. Step 530 involves comparing the magnitude of second current sensed as part of second fault test to a specified current threshold, which can be the same threshold referred to at step 512, but that need not be the case. The order of steps 528 and 530 can be reversed, or steps 528 and 530 can be performed at the same time.

At step 532 there is a determination of whether the second voltage sensed as part of second fault test is less than the specified voltage threshold, and whether the magnitude of second current sensed as part of second fault test is greater than the specified current threshold. Step 532 can be broken into two or more steps.

If the answer to the determination at step 532 is Yes, then flow goes to step 534, and there is a determination that the second fault test passed. In other words, the second fault test is passed if both of the following conditions are true: the second voltage sensed as part of second fault test is less than the specified voltage threshold; and the magnitude of second current sensed as part of second fault test is greater than the specified current threshold. If both the first and second faults test are passed, then the signal generator can be safely used for producing and delivering a treatment signal to patient tissue.

If the answer to the determination at step 532 is No, then flow goes to step 536 and there is a determination that the second fault test failed. In other words, the second fault test is failed if at least one of the following conditions are not true: the second voltage sensed as part of second fault test is less than the specified voltage threshold; or the magnitude of second current sensed as part of second fault test is greater than the specified current threshold. If the second fault test is failed, then there can be a determination as to why the second fault test failed. Details of a method for determining why the second fault test failed are discussed below with reference to FIG. 5D.

Figure 5C:
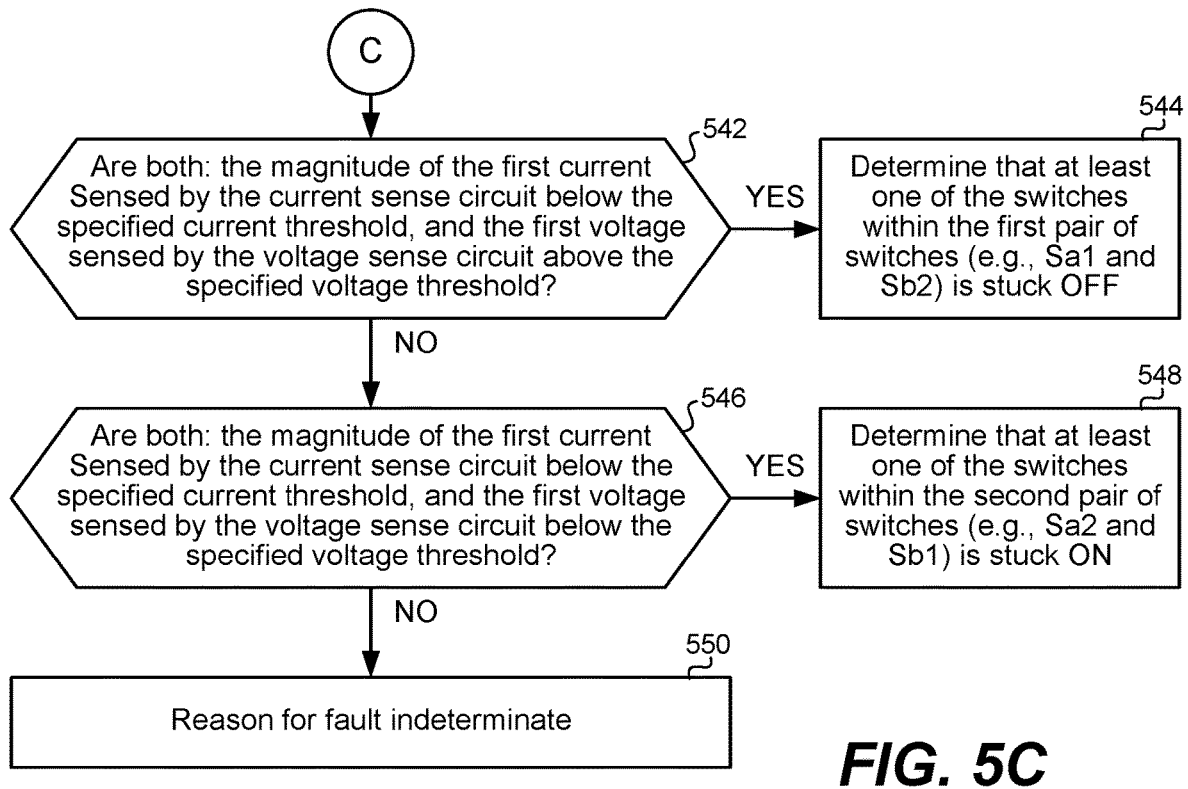
FIG. 5C is a high level flow diagram that is used to summarize a method for determining a reason why the first fault test, discussed with reference to FIGS. 2B and 5A, failed.

FIG. 5C is a high level flow diagram that is used to summarize a method for determining a reason why the first fault test, discussed with reference to FIGS. 2B and 5A, was not passed (i.e., failed). Referring to FIG. 5C, at step 542 there is a determination of whether both of the following conditions associated with the first fault test are true: the magnitude of the first current sensed by the current sense circuit is below the specified current threshold; and the first voltage sensed by the voltage sense circuit above the specified voltage threshold. If the answer to the determination at step 542 is Yes, then flow goes to step 544. At step 544 there is a determination that at least one of the switches within the first pair of switches (e.g., Sa1 and Sb2) is stuck OFF. Such information can be displayed or otherwise provide to a physician or technician, or some other user, via a display, a printout, or via some other user interface.

If the answer to the determination at step 542 is No, then flow goes to step 546. At step 546 there is a determination of whether both of the following conditions associated with the first fault test are true: the magnitude of the first current sensed by the current sense circuit is below the specified current threshold; and the first voltage sensed by the voltage sense circuit below the specified voltage threshold. If the answer to the determination at step 546 is Yes, then flow goes to step 548. At step 548 there is a determination that at least one of the switches within the second pair of switches (e.g., Sa2 and Sb1) is stuck ON. Such information can be displayed or otherwise provide to a physician or technician, or some other user, via a display, a printout, or via some other user interface. If the answer to the determination at step 546 is No, then flow goes to step 550, and the reason that the first fault test failed is indeterminate. The order of steps 542 and 546 can be reversed.

Figure 5D:
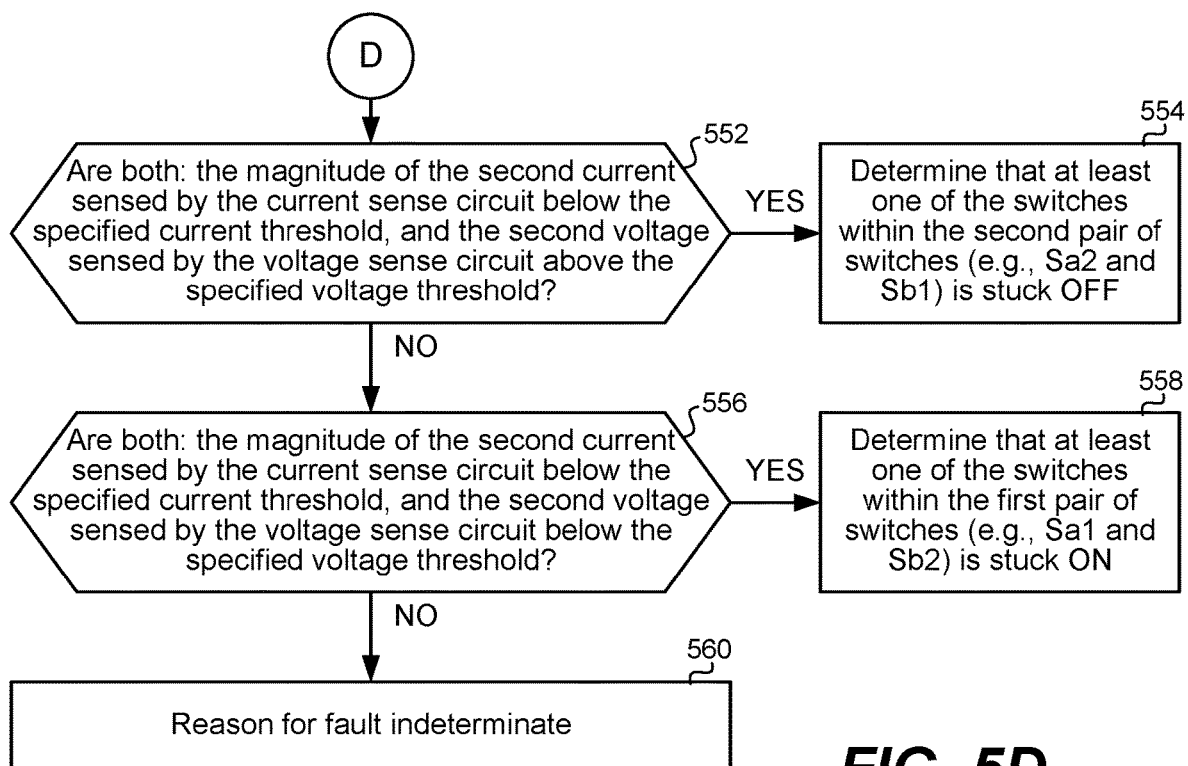
FIG. 5D is a high level flow diagram that is used to summarize a method for determining a reason why the second fault test, discussed with reference to FIGS. 2C and 5B, failed.

FIG. 5D is a high level flow diagram that is used to summarize a method for determining a reason why the second fault test, discussed with reference to FIGS. 2C and 5B, was not passed (i.e., failed). Referring to FIG. 5D, at step 552 there is a determination of whether both of the following conditions associated with the second fault test are true: the magnitude of the second current sensed by the current sense circuit is below the specified current threshold; and the second voltage sensed by the voltage sense circuit is above the specified voltage threshold. If the answer to the determination at step 552 is Yes, then flow goes to step 554. At step 554 there is a determination that at least one of the switches within the second pair of switches (e.g., Sa2 and Sb1) is stuck OFF. Such information can be displayed or otherwise provide to a physician or technician, or some other user, via a display, a printout, or via some other user interface.

If the answer to the determination at step 552 is No, then flow goes to step 556. At step 556 there is a determination of whether both of the following conditions associated with the second fault test are true: the magnitude of the second current sensed by the current sense circuit is below the specified current threshold; and the second voltage sensed by the voltage sense circuit is below the specified voltage threshold. If the answer to the determination at step 556 is Yes, then flow goes to step 558. At step 558 there is a determination that at least one of the switches within the first pair of switches (e.g., Sa1 and Sb2) is stuck ON. Such information can be displayed or otherwise provide to a physician or technician, or some other user, via a display, a printout, or via some other user interface. If the answer to the determination at step 556 is No, then flow goes to step 560, and the reason that the first fault test failed is indeterminate. The order of steps 552 and 556 can be reversed.

Referring back to FIGS. 5A and 5B, the fault test described with reference to FIG. 5B can be performed prior to the fault test described with reference to FIG. 5A, in another embodiment. If that were the case, then the fault test described with reference to FIG. 5B can be referred to as the first fault test, and the fault test described with reference to FIG. 5A can be referred to as the second fault test. Other variations are also possible and within the scope of the embodiments described herein.

In the embodiments shown in and described with reference to FIGS. 2B and 2C, the switch Sp is shown as being OFF (i.e., opened) during the first and second fault tests, which means that the HV power supply 202 remains decoupled from the HV capacitor(s) 206 during the first and second fault tests. In such embodiments, the HV capacitor(s) 206 should be charged prior to the first fault test, and should be recharged between the first and second fault tests, in which case the switch Sp should be turned ON for a period of time and then turned OFF prior to the first fault test, and between the first and second fault tests. In alternative embodiments, where the switch Sp remains turned ON (i.e., closed) during the first and second fault tests, the voltage sense circuit 226 will still be able to detect low voltage conditions (i.e., when the voltage sense circuit 226 senses a voltage below the specified voltage threshold), so long as the HV power supply 202 is designed to not supply enough power to keep the HV capacitor(s) 206 charged (above the specified voltage threshold) if one of the switches Sa1, Sa2, Sb1, or Sb2 of the switching network fails (becomes stuck OFF or stuck ON). Instead of (or in addition to) using the switch Sp to control whether the output of the HV power supply 202 is coupled to, or decoupled from, the HV capacitor(s) 206, the output of the HV power supply 202 can be selectively enabled and disabled. Accordingly, where the output of the HV power supply 202 can be selectively enabled and disabled by the controller 204, the switch Sp can optionally be eliminated.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, it is noted that the term "based on" as used herein, unless stated otherwise, should be interpreted as meaning based at least in part on, meaning there can be one or more additional factors upon which a decision or the like is made. For example, if a decision is based on the results of a comparison, that decision can also be based on one or more other factors in addition to being based on results of the comparison.

Embodiments of the present technology have been described above with the aid of functional building blocks illustrating the performance of specified functions and relationships thereof. The boundaries of these functional building blocks have often been defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIGS. 5A through 5D, as well as change the order of various steps. For another example, it is possible to change the boundaries of some of the blocks shown in FIGS. 1A through 2C.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments of the present technology without departing from its scope. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. A signal generator, comprising:
one or more capacitors coupled between a high voltage rail and a low voltage rail and configured to store energy that can be used to selectively generate a treatment signal;
a waveform shaping circuit coupled to the one or more capacitors and including first, second, third, and fourth switches, each of the switches configured to be selectively turned ON and OFF, and each of the switches configured to allow current to pass through the switch when the switch is turned ON and to prevent current from passing through the switch when the switch is turned OFF;
a controller configured to selectively control the switches to selectively turn a first pair of the switches ON and a second pair of the switches OFF during a first period of time, and selectively turn the first pair of the switches OFF and the second pair of the switches ON during a second period of time, in order to generate the treatment signal;
a voltage sense circuit configured to sense a voltage stored on the one or more capacitors; and
a current sense circuit configured to sense a current having a magnitude that is indicative of a magnitude of current flowing through a pair of the switches that are turned ON by the controller;
the controller further configured to
selectively perform a first fault test on the signal generator,
wherein during the first fault test
the first pair of the switches are turned ON,
the second pair of the switches are turned OFF,
the voltage stored on the one or more capacitors, which is sensed by the voltage sense circuit, is compared to a specified voltage threshold, and
the magnitude of the current, which is sensed by the current sense circuit, is compared to a specified current threshold;
determine that the signal generator passed the first fault test in response to both the voltage stored on the one or more capacitors, which is sensed by the voltage sense circuit, being below the specified voltage threshold, and the magnitude of the current, which is sensed by the current sense circuit being above the specified current threshold; and
determine that the signal generator failed the first fault test in response to the magnitude of the current, which is sensed by the current sense circuit being below the specified current threshold.

2. The signal generator of claim 1, wherein as part of the first fault test the controller is configured to:
determine that at least one of the switches within the first pair of the switches is stuck OFF, in response to the magnitude of the current sensed by the current sense circuit being below the specified current threshold, and the voltage sensed by the voltage sense circuit being above the specified voltage threshold; and
determine that at least one of the switches within the second pair of the switches is stuck ON, in response to the magnitude of the current sensed by the current sense circuit being below the specified current threshold, and the voltage sensed by the voltage sense circuit being below the specified voltage threshold.

3. The signal generator of claim 1, wherein the controller is further configured to:
selectively perform a second fault test on the signal generator, wherein during the second fault test the first pair of the switches are turned OFF and the second pair of the switches are turned ON; and
determine that the signal generator passed the second fault test in response to both the voltage sensed by the voltage sense circuit being below the specified voltage threshold, and the magnitude of the current sensed by the current sense circuit being above the specified current threshold; and determine that the signal generator failed the second fault test in response to the magnitude of the current sensed by the current sense circuit being below the specified current threshold.

4. The signal generator of claim 3, wherein as part of the second fault test the controller is configured to:
determine that at least one of the switches within the second pair of the switches is stuck OFF, in response to the magnitude of the current sensed by the current sense circuit being below the specified current threshold, and the voltage sensed by the voltage sense circuit being above the specified voltage threshold; and
determine that at least one of the switches within the first pair of the switches is stuck ON, in response to the magnitude of the current sensed by the current sense circuit being below the specified current threshold, and the voltage sensed by the voltage sense circuit being below the specified voltage threshold.

5. The signal generator of claim 4, wherein the controller is configured to perform at least one of the first and the second fault tests in response to the signal generator being powered on.

6. The signal generator of claim 1, wherein the controller is implemented by at least one of a processor or a field programmable gate array (FPGA).

7. The signal generator of claim 1, wherein:
the first and the second switches are connected in series within a first branch of the waveform shaping circuit;
the third and the fourth switches are connected in series within a second branch of the waveform shaping circuit;
the first and the second branches are parallel to one another;
a first output node of the waveform shaping circuit is between the first and the second switches;
a second output node of the waveform shaping circuit is between the third and the fourth switches;
the first pair of the switches includes the first and fourth switches; and
the second pair of the switches includes the second and third switches.

8. The signal generator of claim 7, wherein:
the first switch is connected between the high voltage rail and the first output node;
the second switch is connected between the first output node and the low voltage rail;
the third switch is connected between the high voltage rail and the second output node; and
the fourth switch is connected between the second output node and the low voltage rail.

9. The signal generator of claim 8, further comprising:
a transformer including first and second primary windings and a secondary winding;
wherein the first and the second primary windings are parallel to one another and coupled between the first and the second output nodes of the waveform shaping circuit; and
wherein the current sensed by the current sense circuit is generated in response to a voltage being induced in the secondary winding and used to produce the treatment signal.

10. The signal generator of claim 1, further comprising:
a transformer including first and second primary windings and a secondary winding;
wherein the first and the second primary windings are parallel to one another and coupled to the waveform shaping circuit; and
wherein the current sensed by the current sense circuit is generated in response to a voltage being induced in the secondary winding and used to produce the treatment signal.

11. A method for use by a signal generator that includes one or more capacitors configured to store energy that can be used to selectively generate a treatment signal, and a waveform shaping circuit coupled to the one or more capacitors and including first, second, third, and fourth switches, each of the switches configured to be selectively turned ON and OFF, and each of the switches configured to allow current to pass through the switch when the switch is turned ON and to prevent current from passing through the switch when the switch is turned OFF;
the method comprising:
performing a first fault test on the signal generator, wherein during the first fault test a first pair of the switches are turned ON and a second pair of the switches are turned OFF;
sensing a first voltage stored on the one or more capacitors, and comparing the first voltage to a specified voltage threshold, as part of the first fault test;
sensing a first current having a magnitude that is indicative of a magnitude of current flowing through the first pair of the switches that are turned ON, and comparing the magnitude of the first current to a specified current threshold, as part of the first fault test; and
determining whether the signal generator passed the first fault test based on a result of the comparing the first voltage stored on the one or more capacitors to the specified voltage threshold, and based on a result of the comparing the magnitude of the first current to the specified current threshold.

12. The method of claim 11, wherein the determining whether the signal generator passed the first fault test comprises:
determining that the signal generator passed the first fault test in response to both the first voltage stored on the one or more capacitors, which is sensed as part of the first fault test being below the specified voltage threshold, and the magnitude of the first current sensed as part of the first fault test being above the specified current threshold.

13. The method of claim 11, wherein the determining whether the signal generator passed the first fault test comprises:
determining that the signal generator failed the first fault test in response to the magnitude of the first current being below the specified current threshold.

14. The method of claim 13, wherein the determining that the signal generator failed the first fault test further comprises:
determining that at least one of the switches within the first pair of the switches is stuck OFF, in response to the magnitude of the first current sensed as part of the first fault test being below the specified current threshold, and the first voltage sensed as part of the first fault test being above the specified voltage threshold; or
determining that at least one of the switches within the second pair of the switches is stuck ON, in response to the magnitude of the first current sensed as part of the first fault test being below the specified current threshold, and the first voltage sensed as part of the first fault test being below the specified voltage threshold.

15. The method of claim 14, wherein
the first and the second switches are connected in series within a first branch of the waveform shaping circuit;
the third and the fourth switches are connected in series within a second branch of the waveform shaping circuit;
the first and the second branches are parallel to one another;
a first output node of the waveform shaping circuit is between the first and the second switches;
a second output node of the waveform shaping circuit is between the third and the fourth switches;
the first pair of the switches includes the first and the fourth switches; and
the second pair of the switches includes the second and the third switches.

16. The method of claim 11, further comprising:
performing a second fault test on the signal generator, wherein during the second fault test the first pair of the switches are turned OFF and the second pair of the switches are turned ON;
sensing a second voltage stored on the one or more capacitors, as part of the second fault test;
sensing a second current having a magnitude that is indicative of a magnitude of current flowing through the second pair of the switches that are turned ON, as part of the second fault test; and
determining whether the signal generator passed the second fault test based on the second voltage stored on the one or more capacitors, and based on the second current having the magnitude that is indicative of the magnitude of current flowing through the second pair of the switches that are turned ON, which are sensed as part of the second fault test.

17. The method of claim 16, wherein the determining whether the signal generator passed the second fault test comprises:
determining that the signal generator passed the second fault test in response to both the second voltage sensed as part of the second fault test being below a specified voltage threshold, and the magnitude of the second current sensed as part of the second fault test being above a specified current threshold.

18. The method of claim 17, wherein the determining whether the signal generator passed the second fault test comprises:
determining that the signal generator failed the second fault test in response to the magnitude of the second current sensed as part of the second fault test being below the specified current threshold.

19. The method of claim 18, wherein the determining that the signal generator failed the second fault test further comprises:
determining that at least one of the switches within the second pair of the switches is stuck OFF, in response to the magnitude of the second current sensed as part of the second fault test being below the specified current threshold, and the second voltage sensed as part of the second fault test being above the specified voltage threshold; or
determining that at least one of the switches within the first pair of the switches is stuck ON, in response to the magnitude of the second current sensed as part of the second fault test being below the specified current threshold, and the second voltage sensed as part of the second fault test being below the specified voltage threshold.

20. A signal generator, comprising:
one or more capacitors configured to store energy that can be used to selectively generate a treatment signal;
a switching network including first, second, third, and fourth switches, the first and the second switches connected in series with one another and in parallel with the one or more capacitors, and the third and the fourth switches connected in series with one another and in parallel with the one or more capacitors;
each switch of the first, second, third, and fourth switches configured to be selectively turned ON and OFF, configured to allow current to pass through the switch when the switch is turned ON, and configured to prevent current from passing through the switch when the switch is turned OFF;
a controller configured to selectively control the switches to selectively turn the first and the fourth switches ON and the second and the third switches OFF during a first period of time, and selectively turn the first and the fourth switches OFF and the second and the third switches ON during a second period of time, in order to generate the treatment signal;
a voltage sense circuit configured to sense a voltage stored on the one or more capacitors; and
a current sense circuit configured to sense current having a magnitude that is indicative of a magnitude of current flowing through the ones of the switches that are turned ON by the controller;
the controller further configured to
selectively perform a first fault test on the signal generator,
wherein during the first fault test
the first pair of the switches are turned ON,
the second pair of the switches are turned OFF,
the voltage stored on the one or more capacitors, which is sensed by the voltage sense circuit, is compared to a specified voltage threshold, and
the magnitude of the current, which is sensed by the current sense circuit, is compared to a specified current threshold;
determine that the signal generator passed the first fault test in response to both the voltage stored on the one or more capacitors, which is sensed by the voltage sense circuit, being below the specified voltage threshold, and the magnitude of the current, which is sensed by the current sense circuit being above the specified current threshold; and
determine that the signal generator failed the first fault test in response to the magnitude of the current, which is sensed by the current sense circuit being below the specified current threshold.

21. The signal generator of claim 20, wherein the controller is further configured to:
selectively perform a second fault test on the signal generator, wherein during the second fault test the first and the fourth switches are turned OFF and the second and the third switches are turned ON; and
determine that the signal generator passed the second fault test in response to both the voltage sensed by the voltage sense circuit being below the specified voltage threshold, and the magnitude of the current sensed by the current sense circuit being above the specified current threshold; and determine that the signal generator failed the second fault test in response to the magnitude of the current sensed by the current sense circuit being below the specified current threshold.

22. The signal generator of claim 21, further comprising:
a first output node between the first and the second switches;
a second output node between the third and the fourth switches;
a transformer including first and second primary windings and a secondary winding;
wherein the first and the second primary windings are parallel to one another and coupled between the first and the second output nodes; and
wherein the current sensed by the current sense circuit is generated in response to a voltage being induced in the secondary winding and used to produce the treatment signal.

\* \* \* \* \*

UNITED STATES PATENT AND TRADEMARK OFFICE
CERTIFICATE OF CORRECTION

PATENT NO. : 11,638,819 B2
APPLICATION NO. : 17/227232
DATED : May 2, 2023
INVENTOR(S) : T. Gundert et al.

Page 1 of 1

It is certified that error appears in the above-identified patent and that said Letters Patent is hereby corrected as shown below:

In the Claims

Column 22, Line 39 (Claim 1), change "circuit" to -- circuit, --

Column 22, Line 43 (Claim 1), change "circuit" to -- circuit, --

Column 26, Line 50 (Claim 20), change "circuit" to -- circuit, --

Column 26, Line 54 (Claim 20), change "circuit" to -- circuit, --

Signed and Sealed this
Tenth Day of October, 2023

Katherine Kelly Vidal
*Director of the United States Patent and Trademark Office*